United States Patent [19]

Lowe, III

[11] Patent Number: 5,162,339

[45] Date of Patent: Nov. 10, 1992

[54] QUINUCLIDINE THERAPEUTIC AGENTS

[75] Inventor: John A. Lowe, III, Stonington, Conn.

[73] Assignee: Pfizer Inc., New York, N.Y.

[21] Appl. No.: 566,338

[22] PCT Filed: Nov. 20, 1989

[86] PCT No.: PCT/US89/05338

§ 371 Date: Jul. 20, 1990

§ 102(e) Date: Jul. 20, 1990

[87] PCT Pub. No.: WO90/05729

PCT Pub. Date: May 31, 1990

[51] Int. Cl.$^5$ .................. C07D 453/02; C07D 239/02; A61K 31/445; A61K 31/505

[52] U.S. Cl. .................................... 514/305; 514/816; 546/133; 546/134; 546/135; 546/136; 424/1.1

[58] Field of Search ............... 546/133, 134, 135, 136; 514/305; 424/1.1

[56] References Cited

U.S. PATENT DOCUMENTS

| | | | |
|---|---|---|---|
| 3,560,510 | 2/1971 | Warawa | 546/133 |
| 3,917,612 | 11/1975 | Grethe et al. | 546/133 |
| 4,657,911 | 4/1987 | Imbert et al. | 546/133 |

OTHER PUBLICATIONS

Snider ". . . Antagonist of Substance P", Science, vol. 251, pp. 435-437, Jan. 25, 1991.

Primary Examiner—Marianne M. Cintins
Assistant Examiner—Catherine Scalzo
Attorney, Agent, or Firm—Peter C. Richardson; Paul H. Ginsburg; Karen DeBenedictis

[57] ABSTRACT

A series of cis-3-[(cyclic)methylamino]-2-[(α-substituted)arylmethyl]quinuclidines, 3-[(cyclic)methylimino]-2-[(α-substituted)-arylmethyl]quinuclidines and cis-3-[(cyclic)-methyleneamino]-2-[(α-substituted)arylmethyl]-quinuclidines, including their pharmaceutically acceptable salts, are disclosed. These particular compounds are found to be useful as substance P antagonists and therefore, are of value in treating gastrointestinal disorders, central nervous system disorders, inflammatory diseases and pain or migraine. Preferred member compounds include cis-3-[(2-chlorophenyl)methylamino]-2-benzhydryl-quinuclidine, cis-3-[(2-trifluorophenyl)methylamino]2-benzhydrylquinuclidine and cis-[(2-methoxyphenyl)methylamino]-2-benzhydrylquinuclidine. Methods for preparing these compounds from known starting materials are provided.

48 Claims, No Drawings

QUINUCLIDINE THERAPEUTIC AGENTS

TECHNICAL FIELD

This invention relates to new and useful quinuclidine derivatives of interest to those in the field of medicinal chemistry and chemotherapy. More particularly, it is concerned with a novel series of cis-3-[(cyclic)methylamino]-2-[(α-substituted)arylmethyl]quinuclidines, 3-[(cyclic)methylimino]-2-[α-substituted)arylmethyl]-quinuclidines and cis-3-[(cyclic)methyleneamino]-2](α-substituted)arylmethyl]quinuclidines, including their pharmaceutically acceptable salts, which are of especial value in view of their ability to antagonize substance P. In this way, these compounds are of use in treating gastrointestinal disorders, central nervous system disorders, inflammatory diseases and pain or migraine. The invention also includes a new method of therapy within its scope.

BACKGROUND ART

E. J. Warawa in U.S. Pat. No. 3,560,510 discloses certain 3-amino-2-benzhydrylquinuclidines as being useful as diuretic agents, with the corresponding unsubstituted 3-benzylamino compounds acting as intermediates for same. Additionally, E. J. Warawa et al. in the *Journal of Medicinal Chemistry*, Vol. 18, p. 587 (1975) extends this work to other members of the series wherein the 3-amino moiety is either ethylamino, β-phenylethylamino, β-isopropylamino or 2-furfurylamino, but in no instance is there any substitution on the phenyl group itself and the 2-benzhydryl moiety is always symmetrically substituted (or unsubstituted). Furthermore, neither of the aforementioned documents teaches or suggests any of these compounds to be useful as substance P antagonists.

Substance P is a naturally occurring undecapeptide belonging to the tachykinin family of peptides, the latter being so-named because of their prompt stimulatory action on smooth muscle tissue. More specifically, substance P is a pharmacologically-active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine [see B. E. B. Sandberg et al., *Journal of Medicinal Chemistry*, Vol. 25, p. 1009 (1982)], as well as in central nervous system disorders such as anxiety and schizophrenia, in respiratory and inflammatory diseases such as asthma and rheumatoid arthritis, respectively, and in gastrointestinal disorders and diseases of the GI tract, like ulcerative colitis and Crohn's disease, etc. (see D. Regoli in "Trends in Cluster Headache," Edited by F. Sicuteri et al., Elsevier Scientific Publishers, Amsterdam, 1987, pp. 85-95).

In the recent past, some attempts have been made to provide peptide-like substances that are antagonists for substance P and other tachykinin peptides in order to more effectively treat the various disorders and diseases listed above. The peptide-like nature of such substances make them too labile from a metabolic point of view to serve as practical therapeutic agents in the treatment of disease. The non-peptidic antagonists of the present invention, on the other hand, do not posses this drawback, being far more stable from a metabolic point of view than the previously-discussed prior art agents.

DISCLOSURE OF THE INVENTION

In accordance with the present invention, it has now been surprisingly found that various novel cis-3-[cyclic]methylamino-2-[(α-substituted)arylmethyl]quinuclidine compounds, as well as the corresponding cis-3-[(cyclic)methylamino]-2-[(α-substituted)arylmethyl]-quinuclidines and cis-3-[(cyclic)methyleneamino]-2-[(α-substituted)arylmethyl]quinuclidines, are useful when employed in therapy as substance P antagonists for treating gastrointestinal disorders, central nervous system disorders, inflammatory diseases and pain or migraine in a mammalian subject so afflicted. More specifically, the novel compounds of this invention are all quinuclidine derivatives of the formulae:

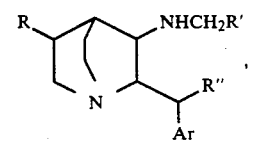

I

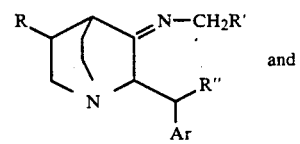

II and

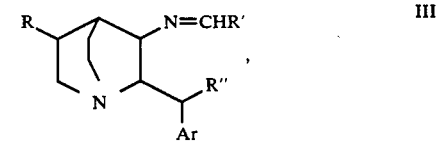

III an include the pharmaceutically acceptable salts thereof, wherein Ar is thienyl, phenyl, fluorophenyl, chlorophenyl or bromophenyl; R is hydrogen or alkyl having from one to four carbon atoms; R' is cycloalkyl having from five to seven carbon atoms, norbornyl, pyrrolyl, 2,3-dihydrobenzofuranyl, thienyl, alkoxythienyl having from one to three carbon atoms in the alkoxy moiety, pyridyl, hydroxypyridyl, quinolinyl, indolyl, naphthyl, alkoxynaphthyl having from one to three carbon atoms in the alkoxy moiety, biphenyl 2,3-methylenedioxyphenyl, or phenyl optionally substituted with up to two substituents selected from cyano, nitro, amino, N-monoalkylamino having from one to three carbon atoms in the alkyl moiety, fluorine, chlorine, bromine, trifluoromethyl, alkyl having from one to three carbons, alkoxy having from one to three carbon atoms, allyloxy, hydroxy, carboxy, alkoxycarbonyl having from one to three carbon atoms in the alkoxy moiety, benzyloxycarbonyl, carboxybenzyloxy, alkoxycarbonylbenzyloxy having from one to three carbon atoms in the alkoxy moiety, carboxamido or N,N-dialkylcarboxamido having from one to three carbon atoms in the alkyl moiety; and R" is branched chain alkyl having from three to four carbon atoms, branched chain alkenyl having from five to six carbon atoms, cycloalkyl having from five to seven carbon atoms, furyl, thienyl, pyridyl, indolyl, biphenyl, or phenyl optionally substituted with up to two substituents selected from fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety or benzyloxycarbonyl, with the proviso that said R" is always other than unsubstituted phenyl, fluorophenyl, chlorophenyl, bromophenyl or alkylphenyl when said R' is unsubstituted phenyl, pyrrolyl or thienyl and Ar is other than thienyl. There is also meant to be included within the purview of this invention stereoisomers and radiolabelled forms of the novel compounds. The compounds of the invention are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal. Additionally, the compounds of formulae II and III are also useful as intermediates for preparing the final products of formula I.

A preferred group of compounds of the present invention of particular interest is that of structural formulae II and III wherein Ar is phenyl, R is hydrogen, R' is 2-chlorophenyl, 2-trifluoromethylphenyl or 2-methoxyphenyl and R" is also phenyl. Another group of preferred compounds of particular interest is that of structural formula I wherein Ar is phenyl, R is hydrogen, R' is phenyl or 2-thienyl and R" is substituted phenyl; especially preferred compounds within the latter group include those wherein R" is 3-methoxyphenyl or 4-methoxycarbonylphenyl. Still another group of preferred compounds of the present invention of particular interest is that of structural formula I wherein Ar is phenyl, R is hydrogen, R' is pyridyl, indolyl or substituted phenyl and R" is also phenyl; especially preferred compounds within this group include those where R' is 4-pyridyl, 3-indolyl, fluorophenyl, difluorophenyl, chlorophenyl, trifluoromethylphenyl, $C_1$-$C_3$ alkylphenyl such as 4-methylphenyl, $C_1$-$C_3$ alkoxyphenyl such as methoxyphenyl, and $C_1$-$C_3$ alkoxycarbonylphenyl such as 4-methoxycarbonylphenyl. The preferred configuration for compounds of structural formulae I and III is cis with respect to the substituents located at the 2- and 3-positions of the quinuclidine nucleus.

Of especial interest in this connection are such typical and preferred member compounds of the invention as cis-3-[(2-chlorophenyl)methylamino]-2-benzhydrylquinuclidine, cis-3-[(2-trifluoromethylphenyl)methylamino]-2-benzhydrylquinuclidine and cis-3-[(2-methoxyphenyl))methylamino]-2-benzhydrylquinuclidine, and their pharmaceutically acceptable acid addition salts. These key compounds of value when employed in therapy for the various reasons previously discussed.

There is also included within the purview of this invention various novel pharmaceutical compositions useful for treating gastrointestinal disorders, central nervous system disorders, inflammatory diseases and pain or migraine in a mammal in need of such treatment, comprising a pharmaceutically acceptable carrier or diluent and a therapeutically-effective amount of a compound selected from the group of quinuclidine derivatives having the formula I, II or III, or a pharmaceutically salt thereof, wherein Ar, R, R' and R" are each as previously defined, with the proviso that said R" is always other than unsubstituted phenyl, fluorophenyl, chlorophenyl, bromophenyl or alkylphenyl when said R' is unsubstituted phenyl, pyrrolyl or thienyl and Ar is other than thienyl. Additionally, there is also meant to be included pharmaceutical compositions of the same type wherein the active ingredient, as previously defined, is present in an amount that is effective for antagonizing the effects of substance P at its receptor site in said mammal.

There is also further included within the purview of this invention a novel method for treating gastrointestinal disorders, central nervous system disorders, inflammatory diseases and pain or migraine in a mammal in need of such treatment, which comprises administering to said mammal a therapeutically-effective amount of a compound selected from the group of quinuclidine derivatives having the formula I, II or III, or a pharmaceutically acceptable salt thereof, wherein Ar, R, R' and R" are each as previously defined, but without the aforesaid proviso. Additionally, there is also included within the purview of the invention a novel method for antagonizing the effects of substance P at its receptor site in a mammal in need of such treatment, which comprises administering to said mammal a compound selected from the group of quinuclidine derivatives having the formula I, II or III, or a pharmaceutically acceptable salt thereof, wherein Ar, R, R' and R" are each as previously defined, but without the aforesaid proviso, in an amount that is effective for antagonizing the effects of substance P at its receptor site in said mammal. Thus, the novel method of treatment aspect of the present invention necessarily encompasses the use of both old and new compounds for the present purposes at hand, inasmuch as it additionally includes the new use of known compounds of structural formulae I, II and III such as those wherein Ar is unsubstituted phenyl, R is hydrogen, R' is unsubstituted phenyl, 2-pyrrolyl or 2-thienyl and R" is also unsubstituted phenyl.

DETAILED DESCRIPTION

In accordance with the process employed for preparing the novel cis-3-[(cyclic)methylamino]-2[(α-substituted)-arylmethyl]quinuclidine compounds of formula I of this particular invention, a cis-3-[(cyclic)methylamino]-2-[(α-substituted)-arylmethyl]quinuclidine compound of the formula II or a cis-3-[(cyclic)methylamino] -2-[(α-substituted)-arylmethyl]quinuclidine compound of the formula III, wherein Ar, R, R' and R" are each as previously defined with the aforesaid proviso, is subjected to the selective reducing action of a suitable metallo reducing agent such as a metal hydride like a borane hydride, alane hydride or a metal hydride complex like lithium aluminum hydride or sodium borohydride, or an organo-metallic complex such as borane-methyl sulfide, 9-borabicyclononane (9-BBN), triethylsilane and the like. In general, the reduction step is carried out in a reaction-inert organic solvent at a temperature that is in the range of from about 0° C. up to about 120° C. until the reduction step to form the desired cis-3-[(cyclic)methylamino]-2[(α-substituted)-arylmethyl]quinuclidine final product is substantially complete. The preferred reaction temperature for the reduction step is often at the lower end of the aforesaid range, e.g., at about 15°-40° C., with a temperature at or near room temperature (ca. 20° C.) usually being most preferred. The reaction pressure is not critical, e.g., a reaction pressure of about 0.5 to about 2.0 atmospheres is generally employed, with the preferred pressure usually being at or near ambient pressure (i.e., at about one atmosphere). Preferred reaction-inert organic solvents for use in this connection include polar protic solvents such as methanesulfonic acid and trifluoroacetic acid in the case of triethylsilane, and polar or non-polar aprotic solvents such as acetonitrile, dimethylformamide, diethylformamide, dimethylacetamide, benzene and ethers like diethyl ether, di-isopropyl ether, di-n-butyl ether, tetrahydrofuran, dioxane and 1,2-dimethoxyethane (glyme) and dimethylcellosolve in the case of the other metal hydrides. A preferred embodiment involves the use of 9-borabicyclononane as the reducing agent in an ethereal solvent medium, such as a cyclic ether like tetrahydrofuran or dioxane, or a glycol-derived ether like 1,2-dimethoxyethane at a temperature ranging from about room temperature (ca. 20° C.) up to the reflux temperature of the reaction mixture. In this way, the desired cis-isomer of the final product is produced with a high degree of selectivity. Upon completion of the reduction step, the desired methylamine final product is readily recovered from the reaction mixture by any number of conventional procedures well-known to those skilled in the art.

The novel 3-[(cyclic)methylamino]-2-[(α-substituted)-arylmethyl]quinuclidine compounds of formula II, which are required for preparing the novel final products of formula I, are also useful as substance P antagonists. They are, in turn, prepared by condensing a corresponding 2-[(α-substituted)arylmethyl]quinuclidine-3-one compound of the formula IV:

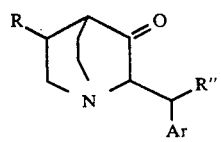

IV wherein Ar, R and R" are each defined as aforesaid, with a (cyclic)methylamine of the formula R'CH$_2$NH$_2$, wherein R' is also defined as before, to form the desired imine final product of structural formula II. This particular reaction is normally carried out by heating the two reactants together at a elevated temperature in a reaction-inert organic solvent, such as an aromatic hydrocarbon solvent like benzene, toluene and xylene, and preferably in the presence of a catalytic amount of a suitable acidic condensing agent like p-toluene-sulfonic acid or camphorsulfonic acid, such that the water formed as a byproduct in the reaction is thereafter immediately collected as it distills over at the boiling point of the solvent. Alternatively, the reaction can also be carried out by using a dehydrating agent like titanium tetrachloride in a suitable reaction-inert organic solvent, such as a cyclic ether like tetrahydrofuran or dioxane. Either way, the overall general condensation reaction is usually conducted at a temperature that is in the range of from about 35° C. up to about 140° C. and preferably at about 65°–110° C. until the condensation is substantially complete, i.e., until no more water of reaction forms, and this will usually require a period of at least about one hour and preferably up to about 18–24 hours. Although substantially equimolar proportions of reactants are normally required, it is preferable in practice to employ an excess of the (cyclic)methylamine base, e.g., up to about 2.0 mole of amine per mole of 2-[(α-substituted)arylmethyl]quinuclidin-3-one starting material, in order to ensure completeness of reaction without causing unwanted side reactions to occur to any significant degree. Upon completion of the reaction, the desired methylimine final product is then easily isolated form the reaction mixture in a conventional manner; e.g., by first concentrating said mixture in vacuo and thereafter triturating the residue with a suitable solvent such as isopropanol, followed by recrystallization from the same solvent or tetrahydrofuran if necessary, or else used as such in the next and final reduction step to afford the desired methylamine final product without any further purification first being employed.

The starting materials required for preparing the novel 3-[(cyclic)methylamino]-2-[(α-substituted)arylmethyl]quinuclidine formula II compounds of this invention are either known compounds which are readily available commercially like many of the amines of formula R'CH$_2$NH$_2$ (e.g., benzylamine or cyclohexylamine, etc.), or they are described in the literature like 2-benzhydrylquinuclidin-3-one (see E. J. Warawa in U.S. Pat. No. 3,560,510), or else they can easily be synthesized by those skilled in the art starting from common chemical reagents and using conventional methods of organic synthesis. For instance, the 2-[(α-substituted)arylmethyl]quinuclidin-3-one compounds are readily prepared from the known quinuclidin-3-one [C. R. Clemo et al., in the *Journal of the Chemical Society* (London), p. 1241 (1939)] via a two-step reaction sequence involving (1) condensation with an appropriate aldehyde compound of the formula R"CHO to form the corresponding 2-(α-substituted)methylidenequinuclidin-3-one, followed by (2) treatment of the latter intermediate with arylmagnesium bromide, such as phenylmagnesium bromide, in a Grignard reaction to yield the desired 2-[(α-substituted)arylmethyl]-quinuclidin-3-one starting material (e.g., see Preparations A–C in this regard).

The novel cis-3-[(cyclic)methyleneamino]-2-[(α-substituted)arylmethyl]quinuclidine compounds of formula III, which are also used to prepare the novel final products of formula I and are also additionally useful as substance P antagonists, are prepared by condensing a corresponding 3-amino-2-[(α-substituted)phenylmethyl]quinuclidine compound of the formula V:

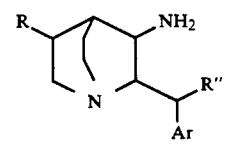

V wherein Ar, R and R" are each defined as aforesaid, with an appropriate cyclic aldehyde compound of the formula R'CHO, wherein R' is also defined as before, to form the desired methyleneamine final product of structural formula III. This particular reaction is normally carried out in the same manner as that described previously for the condensation reaction between the quinuclidin-3-ones of formula IV and the amines of formula R'CH$_2$NH$_2$ to form the imines of formula II, except that in the present instance it is preferable to employ an excess of the R'CHO aldehyde reagent rather than the 3-amino base compound, in order to ensure completeness of reaction with little or no byproduct formation that could possibly contaminate the desired final product of structural formula III. In practice, it has been found most convenient to use up to about 3.0–6.0 mole of cyclic aldehyde per mole of 3-amino-2-[(α-substituted)arylmethyl]quinuclidine starting material for the present purposes at hand. Upon completion of the reaction, the desired methyleneamine final product is either isolated and purified as such in the same manner as that described previously for the corresponding methylimine compound, or else used as the key substrate without any further purification in the next and final reduction step to form the desired methylamine final product of structural formula I.

The starting materials required for preparing the novel cis-3-[(cyclic)methyleneamino]-2-[(α-substituted-)arylmethyl]quinuclidine compounds of formula III are either known compounds which are readily available commercially like many of the aldehydes of formula R'CHO (e.g., 2,6-dichlorobenzaldehyde), or they are described in the literature like 3-amino-2-benzhydrylquinuclidine [E. J. Warawa et al., in the *Journal of Medicinal Chemistry*, Vol. 18, p. 587 (1975)], or else they can easily by synthesized by those skilled in the art starting from common chemical reagents and using conventional methods of organic synthesis. For instance, the 3-amino-2-[(α-substituted)arylmethyl]quinuclidine compounds are readily prepared from the corresponding 3-benzylamino compounds of formula I by treating the latter type compounds with ammonium formate in the presence of a noble metal catalyst, such as palladium-on-carbon (preferably about 10% by weight), in a reaction-inert organic solvent, such as a lower alkanol like methanol, ethanol or isopropanol, at a temperature ranging from about 20° C. up to about 100° C. and preferably at the reflux temperature of the reaction mixture.

Additionally, the cis-3-[(cyclic)]methyleneamino-2-[(α-substituted)arylmethyl]quinuclidine final products of formula I can also be prepared by another alternate route which involves subjecting a corresponding 3-[(cyclic)carbonylamino]-2-[(α-substituted)arylmethyl]-quinuclidine compound of the formula:

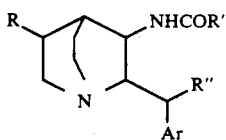

to the selective reducing action of a suitable metallo reducing agent such as a metal hydride like a borane hydride, alane hydride or hydride complex like lithium aluminum hydride, or an organo-metallic complex such as borane-methyl sulfide and the like. This particular reaction is normally carried out in the same manner as that described previously for the reduction of the corresponding formula II methylimines and the formula III methyleneamine compounds to form the methylamine final products of formula I, except that in the present case the reaction temperature is usually in the range of from about 20° C. up to about 120° C., with the preferred temperature often being found in the neighborhood of the near upper end of the aforesaid range, e.g., at about 65°-100° C., with a temperature at or near the reflux temperature of the reaction mixture usually being most preferred. Upon completion of the reduction reaction, the desired methylamine final product of formula I is readily recovered from the reaction mixture in essentially the same manner as before.

The 3-[(cyclic)carbonylamino]-2-[(α-substituted)arylmethyl]quinuclidines of formula VI, which are required as starting materials for preparing the novel final products of formula I, are, in turn, prepared from the previously-discussed corresponding 3-amino-2-[(α-substituted)arylmethyl]quinuclidines of formula V by reacting same with an activated derivative of a known carboxylic acid of the formula R'COOH. This is readily accomplished by first activating said acid compound of formula R'COOH by converting it into a derivative such as the acid chloride, the acyl imidazole or the acyl azide, using conventional methods or organic synthesis well-known to those skilled in the art. For example, the acid can be first reacted in a reaction-inert organic solvent, such as dioxane tetrahydrofuran, diethyl ether, 1,2-dimethoxyethane-(glyme) or methylene chloride, with an activating agent such as thionyl chloride, carbonyl di-imidazole or diphenyl phosphoryl azide, as the case may be, optionally in the presence of an organic base such as triethylamine, at a temperature ranging from ambient (ca. 20° C.) to the reflux temperature of the reaction mixture (e.g., at about 20°-80° C.), with the preferred reaction temperature being in the neighborhood of the lower limit of the aforesaid range (e.g., at about 20°-35° C.). Upon completion of this particular reaction step, the compound of formula V is next added to the mixture and the reaction continued at a temperature of from about 65° C. up to about 100° C., and preferably at the reflux temperature of the mixture, until the production of the desired 3-(cyclic)carbonylamino derivative is substantially complete (and this will usually require a period of at least about one-half hour and sometimes up to as long as 24 hours). At this point, the desired 3-(cyclic)carbonylamino derivative is readily recovered from the reaction mixture in a conventional manner and thereafter reduced to the corresponding 3-(cyclic)methylamine compound, i.e., the methylamine final product of formula I, in the manner previously described.

As regards compounds of the invention of structural formula I wherein R' is aminophenyl, these can readily be prepared from the corresponding compounds of structural formula I where R' is nitrophenyl by simply subjecting the latter to catalytic hydrogenation in the presence of a noble metal catalyst (e.g., palladium-on-carbon catalyst), preferably using a lower alkanol solvent medium such as methanol, ethanol or isopropanol, according to methods well-known to those skilled in the art. In this way, cis-3-[(2-methoxy-5-nitrophenyl)methylamino]-2-benzhydrylquinuclidine is readily converted to the corresponding 5-aminophenyl compound.

Inasmuch as the quinuclidine compounds of this invention all possess at least one asymmetric center, they are capable of occurring in various stereoisomeric forms or configurations. Hence, the compounds can exist in separated (+)- and (−)-optically active forms, as well as in racemic or (±)-mixtures thereof, and in the case of those compounds with two asymmetric centers, they can additionally exist as diastereomers with respective optical isomers thereof. The present invention is meant to include all such forms within its scope. For instance, the diastereomers can be separated by methods well known to those skilled in the art, e.g., by fractional crystallization and the like, while the optically-active isomers can be obtained by simply resolving the racemates via the standard procedures of organic chemistry that are known for these purposes.

The radiolabelled quinuclidine compounds of the formulas, I, II and III are useful as research and diagnostic tools in metabolism pharmacokinetic studies and in binding assays with the drug in both animal and man. Specific applications in research include radioligand binding assays, autoradiography studies and in vivo binding studies, while specific applications in the diagnostic area include studies of the substance P receptor in the human brain, such as up/down regulation in a disease state, and in vivo binding in the relevant tissues for inflammation, e.g., immune-type cells or cells that are directly involved in inflammatory bowel disorders and the like. Specifically, included among the radiolabelled forms of the quinuclidine compounds of formulas I, II and III are the tritium and $C^{14}$-isotopes of (−)-cis-3-[(2-methoxyphenyl)methylamino]-2-benzhydrylquinuclidine.

Insofar as the majority of the 3-methylamino-2-[(α-substituted)arylmethyl]quinuclidine compounds of formula I of this invention are basic compounds, as are the corresponding methylimines and methyleneamines of formulas II and III, they are all capable of forming a wide variety of different salts with various inorganic and organic acids. Although such salts must be pharmaceutically acceptable for administration to animals, it is often desirable in practice to initially isolate the quinuclidine base compound from the reaction mixture as a pharmaceutically unacceptable salt and then simply convert the latter back to the free base compound by treatment with an alkaline reagent and thereafter, subsequently convert the latter free base to a pharmaceutically acceptable acid addition salt. The acid addition salts of the quinuclidine base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The acids which are used to prepare the pharmaceutically acceptable acid addition salts of the aforementioned quinuclidine base compounds of this invention are those which form non-toxic acid addition salts, i.e., salts containing pharmacologically acceptable anions, such as the hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)] salts.

Those quinuclidine compounds of the invention which are also acidic in nature, e.g., where R" is carboxyphenyl, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic quinuclidine derivatives. These particular non-toxic base salts include those derived from such pharmacologically acceptable cations as sodium, potassium, calcium and magnesium, etc. These salts can easily be prepared by treating the aforementioned acidic quinuclidine compounds with an aqueous solution containing the desired pharmacologically acceptable cation, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The active quinuclidine compounds of the present invention, i.e., those of structural formulas I, II and III, wherein Ar, R, R' and R" are each as previously defined (without proviso), exhibit significant substance P receptor-binding activity and therefore, are of value in the treatment of a wide variety of clinical conditions which are characterized by the presence of an excess of said substance P activity. Such conditions include gastrointestinal disorders such as ulcer and colitis and other like diseases of the gastrointestinal tract, central nervous system disorders such as anxiety and psychosis, inflammatory diseases such as rheumatoid arthritis and inflammatory bowel diseases, respiratory diseases such as asthma, as well as pain in any of the aforesaid conditions, including migraine. Hence, these compounds are readily adapted to therapeutic use as substance P anatagonists for the control and/or treatment of any of the aforesaid clinical conditions in mammals, including humans. For instance, cis-3-[(2-chlorophenyl)methylamino]-2-benzhydrylquinuclidine, a preferred compound of the present invention, when tested as an anti-inflammatory agent exhibits a significant degree of activity in the standard carrageenin-induced rat foot edema test [described by C. A. Winter et al., *Proceedings of the Society of Experimental Biology and Medicine,* Vol. 111, p. 544 (1962)], where it was found to cause a 50% inhibition in swelling at the 100 mg./kg. dose level when given by the oral route. Moreover, when tested as an anti-psychotic agent, this same compound was found to produce a 50% inhibition of substance P-induced locomotion in rats at the 32 mg./kg. dose level when given by the intraperitoneal route.

The active quinuclidine compounds hereinbefore described can be administered via either the oral, parenteral or topical routes. In general, these compounds are most desirably administered in doses ranging from about 5.0 mg. up to about 1500 mg. per day, although variations will necessarily occur depending upon the weight and condition of the subject being treated and the particular route of administration chosen. However, a dosage level that is in the range of from about 0.07 mg. to about 21 mg. per kg. of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The compounds of the present invention may be administered alone or in combination with pharmaceutically acceptable carriers or diluents by either of the three routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention, as substance P antagonists, is determined by their ability to inhibit the binding of substance P at its receptor sites in bovine caudate tissue, employing radioactive ligands to visualize the tachykinin receptors by means of autoradiography. The substance P antagonist activity of the herein described quinuclidine compounds is evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

The anti-inflammatory activity of the compounds of the present invention is demonstrated in the previously mentioned standard carrageenin-induced rat foot edema test. In this test, anti-inflammatory activity is determined as the percent inhibition of edema formation in the hind par of male albino rats (weighing 150–190 g.) in response to a sub-plantar injection of carrageenin. The carrageenin is injected as a 1% aqueous solution. Edema formation is then assessed by measuring the volume of the injected paw initially as well as three hours after the carrageenin injection. The increase in volume three hours after carrageenin injection constitutes the individual response. Compounds are considered active if the difference in response between the drug-treated animals (six rats/group) and a control group receiving the vehicle alone is significant on comparison with the results afforded by a standard compound like phenylbutazone at 33 mg./kg., via the oral route of administration.

The anti-psychotic activity of the compounds of the present invention as neuroleptic agents for the control of various psychotic disorders is determined primarily by a study of their ability to suppress substance P-induced hypermotility in rats. This study is carried out by first dosing the rats with a control compound or with an appropriate test compound of the present invention, then injecting the rats with substance P by intracerebral administration via canula and thereafter measuring their individual locomotor response to said stimuli.

PREPARATION A

In a 50 ml. round-bottomed reaction flask equipped with reflux condenser and nitrogen-inlet tube, there were placed 5.28 g. (0.04258 mole) of quinuclidin-3-one [C. R. Clemo et al., in the *Journal of Chemical Society* (London), p. 1241 [1939], 11.18 g. (0.06387 mole) of 2,4-dichlorobenzaldehyde, 340 mg. (0.00852 mole) of sodium hydroxide and 21 ml. of ethanol. The resulting reaction mixture was next refluxed for a period of 40 minutes, then cooled to ambient temperatures and the precipitated product subsequently recovered by means of suction filtration. After washing the latter material with ethanol and vacuum drying to constant weight, there were ultimately obtained 8.71 g. (70%) of pure 2,4-dichlorobenzylidenequinuclidin-3-one in the form of a yellow solid melting at 117°–119° C.; IR (cm.$^{-1}$, KBr) 1710, 1700 (C=O). The pure product was further characterized by means of mass spectrum analysis and nuclear magnetic resonance data.

Mass Spectrum (%): 281/283/285 (parent, 2.5 for 281), 248(34), 246(78), 220(26), 218(100), 192(25), 190(60), 186(27), 184(40), 172(25), 164(24), 162(24), 149(24), 136(26), 135(24), 172(32), 126(24), 123(26), 114(26), 99(26), 55(40), 53(22).

NMR Data: $^1$H-NMR ($\delta$, CDCl$_3$) 1.9–2.0 (m, 4H), 2.49 (m, 1H), 2.8–3.2 (m, 4H), 7.1–7.3 and 8.4–8.5 (m, 8H).

PREPARATION B

In a 250 ml. round-bottomed reaction flask equipped with magnetic stirring bar and nitrogen-inlet tube, there were placed 15 ml. (0.04575) of a 1.5M solution of phenylmagnesium bromide in diethyl ether and 76 ml. of dry toluene. Stirring was commenced and the solution was cooled to 0° C., while 8.57 g. (0.03049 mole) of 2,4-dichlorobenzylidenequinuclidin-3-one (the product of Preparation A) in 10 ml. of toluene were added thereto in a dropwise manner. The reaction mixture was then warmed to room temperature (ca. 20° C.) and allowed to stir for a period of 14 hours before finally being quenched with aqueous ammonium chloride. This resulted in the formation of two layers which were then separated, and the separated aqueous layer was next extracted with fresh methylene chloride. The resulting organic layers were then combined and subsequently dried over anhydrous sodium sulfate. After removal of the drying agent by means of filtration and the solvent by means of evaporation under reduced pressure, there was finally obtained a solid residual product which subsequently crystallized from ethanol to afford 6.70 g. (61%) of pure 2-[(2,4-dichlorophenyl)phenylmethyl]-quinuclidin-3-one in the form of a white solid melting at 144°-152° C.; IR(cm.$^{-1}$, KBr), 1725(C=O). The pure product was further characterized by means of mass spectrum analysis and nuclear magnetic resonance data.

Mass Spectrum (%): 360/362/364 (parent, 1.5 for 360), 333(24), 331(27), 292(22), 290(33), 227(26), 214(26), 199(23), 178(64), 177(22), 176(26), 172(43), 165(72), 164(23), 161(56), 159(84), 131(30), 130(34), 91(100), 77(29), 68(22), 55(54).

NMR Data: $^1$H-NMR ($\delta$, CDCl$_3$) 1.9–2.1 (m, 4H), 2.44 (m, 1H), 2.6–2.8 (m, 2H), 2.9–3.1(m, 2H), 3.85(d, 1H), 5.12(d, 1H), 7.1–7.4 (m, 8H).

PREPARATION C

The reaction procedures described in Preparations A-B are repeated to prepare the following 2[($\alpha$-substituted)phenylmethyl]quinuclidin-3-one compounds, starting from quinuclidin-3-one and the requisite organic aldehyde and proceeding thru the corresponding 2-[($\alpha$-substituted)benzylidene]quinuclidin-3-one intermediate in every instance, using the same molar proportions as before:

2-[(3-methoxyphenyl)phenylmethyl]quinuclidin-3-one

2-[(3-methoxycarbonylphenyl)phenylmethyl]quinuclidin-3-one

2-[(2,3-dichlorophenyl)phenylmethyl]quinuclidin-3-one

2-[(2,4-difluorophenyl)phenylmethyl]quinuclidin-3-one

2-[(3-trifluoromethylphenyl)phenylmethyl]quinuclidin-3-one

2-[(2-furyl)phenylmethyl]quinuclidin-3-one

2-[(3,4-dichlorophenyl)phenylmethyl]quinuclidin-3-one

2-[(4-pyridyl)phenylmethyl]quinuclidin-3-one

2-[(E- and Z-2-tert.butylvinyl)phenylmethyl]quinuclidin-3-one

2-[(2-methoxyphenyl)phenylmethyl]quinuclidin-3-one

2-[(2-n-propylphenyl)phenylmethyl]quinuclidin-3-one

2-[(4-carboxyphenyl)phenylmethyl]quinuclidin-3-one

2-[(2-thienyl)phenylmethyl]quinuclidin-3-one

2-[(2-biphenyl)phenylmethyl]quinuclidin-3-one

2-[(3-pyridyl)phenylmethyl]quinuclidin-3-one

2-[(cyclohexyl)phenylmethyl]quinuclidin-3-one.

2-benzhydryl-5-ethylquinuclidin-3-one

PREPARATION D

In a 50 ml. round-bottomed reaction flask equipped with reflux condenser, magnetic stirring bar and nitrogen-inlet tube, there were placed 805.9 mg. (0.005757 mole) of 2-norbornanecarboxylic acid, 932.6 mg. (0.005757 mole) of carbonyldiimidazole and 19 ml. of dry tetrahydrofuran. The reaction mixture was next stirred at room temperature (ca. 20° C.) for a period of 30 minutes, followed by the addition thereto of 1.1207 g. (0.003838 mole) of 3-amino-2-benzhydrylquinuclidine [E. J. Warawa et al., in the *Journal of Medicinal Chemistry*, Vol. 18, p. 71 (1975)]. The resulting mixture was then refluxed for a period of 18 hours, cooled to ambient temperatures and thereafter partitioned between water and methylene chloride. The separated organic layer was next washed with brine and then dried over anhydrous sodium sulfate. After removal of the drying agent by means of filtration and the solvent by means of evaporation under reduced pressure, there was finally obtained a solid residual product which subsequently crystallized from isopropanol to yield 963 mg. (61%) of pure cis-3(2-norbornylcarbonylamino)-2-benzhydrylquinuclidine in the form of a white solid melting at 203°-207° C.; IR (cm.$^{-1}$, KBr) 1645(C=O). The pure product was further characterized by means of mass spectrum analysis and nuclear magnetic resonance data, in addition to elemental analysis.

Mass Spectrum (%): 414 (29, parent), 291(23), 248(31), 247(100), 181(28), 180(96), 167(22), 165(20), 125(28), 97(30), 96(25), 95(77), 91(34), 69(21), 67(26).

NMR Data: $^1$H-NMR ($\delta$, CDCl$_3$) 0.8–3.1 (several multiplets, 19H), 3.94(m, 2H), 4.14 (m, 1H), 4.35(m, 1H), 5.6–5.8 (m, 1H), 7.0–7.4(m, 10H).

Anal. Calcd. for C$_{28}$H$_{34}$N$_2$O 0.5H$_2$O: C. 79.39; H, 8.33; N, 6.61. Found: C, 79.33; H, 8.13; N, 6.72.

PREPARATION E

The procedure described in Preparation D was repeated to prepare the following cis-3-(homocycliccarbonylamino)-2-benzhydrylquinuclidines, starting from the corresponding homocyclic-carboxylic acid and 3-amino-2-benzhydrylquinuclidine in each instance, and using the same molar proportions as before:

cis-3-(1-norbornylcarbonylamino)-2-benzhydrylquinuclidine, m.p. 220°-230° C.

cis-3-(2-benzylphenylcarbonylamino)-2-benzhydrylquinuclidine, m.p. 215°-222° C.

cis-3-(3,5-difluorophenylcarbonylamino)-2-benzhydrylquinuclidine, m.p. 225°-230° C.

cis-3-(2,3-difluorophenylcarbonylamino)-2-benzhydrylquinuclidine, m.p. 250°-256° C.

PREPARATION F cis-3-Benzylamino-2-benzhydrylquinuclidine (m.p. 145°-148° C.) was prepared according to the procedure described by E. J. Warawa et al., as first reported in the *Journal of Medicinal Chemistry*, Vol. 18, p. 587 (1975), wherein 3-keto-2-benzhydrylquinuclidine was condensed with benzylamine and the resultant intermediate, viz., 3-benzylimino-2-benzhydrylquinuclidine, was then reduced with sodium borohydride to afford the desired final product. The melting point of the final product was 151.5°-152° C., according to E. J. Warawa et al.

PREPARATION G cis-3-[(2-Thienyl)methylamino]-2-benzhydrylquinuclidine (m.p. 140°-145° C.) was prepared in accordance with the procedure reported in Preparation F by condensing 3-keto-2-benzhydrylquinuclidine with (2-thienyl)methylamine (i.e., 2-thenylamine), followed by reduction of the resultant intermediate (viz., 3-[(2-thienyl)methylimino]-2-benzhydrylquinuclidine) with sodium borohydride to ultimately afford the desired final product.

PREPARATION H cis-3-[(2-Pyrrolyl)methylamino]-2-benzhydrylquinuclidine (m.p. 137.5°–138.5° C.) was prepared in accordance with the procedure reported in Preparation F by condensing 3-keto-2-benzhydrylquinuclidine with (2-pyrrolyl)methylamine, followed by reduction of the resultant intermediate (viz., 3-[(2-pyrrolyl)methylimino]-2-benzhydrylquinuclidine] with sodium borohydride to ultimately afford the desired final product.

EXAMPLE 1

A. In a 50 ml. round-bottomed reaction flask equipped with a Dean-Stark trap, reflux condenser and nitrogen-inlet tube, there were placed 1.12 g. (0.00385 mole) of 3-keto-2-benzyhydrylquinuclidine [E. J. Warawa et al., *Journal of Medicinal Chemistry*, Vol. 17, p. 497 (1974)], 652 mg. (0.00577 mole) of cyclohexylmethylamine, 17.8 mg. (0.00077 mole) of camphorsulfonic acid and 19 ml. of toluene. The reaction mixture was then refluxed azeotropically (with separation of water) for a period of 18 hours, cooled to ambient temperatures and concentrated in vacuo to afford a solid residue.

B. The residual material obtained above [crude 3-(cyclohexylmethylimino)-2-benzhydrylquinuclidine] was then dissolved in 13 ml. of dry tetrahydrofuran, and the resulting solution was cooled to 0° C., with stirring, while under a dry nitrogen atmosphere. At this point, 10.8 ml. (0.00539 mole) of a 1.5M solution of 9-borabicyclononane (9-BBN) in tetrahydrofuran was added to the chilled solution (with stirring), and the resulting reaction mixture was then allowed to warm to room temperature (ca. 20° C.) and thereafter stirred for a period of three days at ambient temperatures. Upon completion of this step, the stirred reaction mixture was next quenched with water, and then partitioned between aqueous 1N hydrochloric acid and methylene chloride, with the two layers thereafter being separated. The separated aqueous layer was then adjusted to pH 14 with solid sodium hydroxide and thereafter extracted with fresh methylene chloride. The combined organic extracts were subsequently dried over anhydrous sodium sulfate and filtered, and the resulting filtrate thereafter evaporated to dryness while under reduced pressure to afford a solid residual product. Crystallization of the latter material from isopropanol then gave 334 mg. (22%) of pure cis-3-(cyclohexylmethylamino)-2-benzhydrylquinuclidine as white crystals melting at 152°–153° C. The pure product was further characterized by means of mass spectrum analysis and nuclear magnetic resonance data, in addition to elemental analysis.

Mass Spectrum (%): 389(parent+1, <1.0), 274(3), 222(40), 221(100), 178(25), 165(21), 164(24), 154(44), 110(40), 108(21), 97(25), 96(31), 82(35), 70(21), 56(30), 55(33).

NMR Data: $^1$H-NMR ($\delta$, CDCl$_3$) 0.4–0.6 (m, 2H), 1.0–1.2(m, 6H), 1.5–1.7(m, 4H), 1.8–2.0(m, 2H), 2.23(m, 1H), 2.63(t, 1H), 2.7–2.9 (m, 4H), 3.18(m, 1H), 3.69(dd, 1H), 4.42(d, 1H), 7.0–7.4(m, 10H), $^{13}$C-NMR (CDCl$_3$) 20.0, 24.9, 25.5, 25.9, 26.1, 26.6, 30.9, 31.1, 36.9, 41.1, 49.4, 49.6, 55.1, 56.0, 62.0, 126.0, 126.5, 127.5, 128.4, 129.1, 143.2, 145.4.

Anal. Calcd. for $C_{27}H_{36}N_2$: C, 83.45; H, 9.34; N, 7.21. Found: C, 83.20; H, 9.34; N, 7.21.

EXAMPLE 2

The two-step reaction procedure described in Example 1 was repeated except that 2-chlorobenzylamine was the reagent employed in place of cyclohexylamine, using the same molar proportions as before. In this particular case, the corresponding final product obtained was cis-3-[(2-chlorophenyl)methylamino]-2-benzhydrylquinuclidine (yield, 58%), m.p. 172°–174° C.

Anal. Calcd. for $C_{27}H_{29}ClN_2$: C, 77.77; H, 7.01; 6.72. Found: C, 77.34; H, 6.95; N, 6.65.

EXAMPLE 3

The two-step reaction procedure described in Example 1 was repeated except that 2-trifluorobenzylamine was the reagent employed in place of cyclohexylamine, using the same molar proportions as before. In this particular case, the corresponding final product obtained was cis-3-[(2-trifluorophenyl)methylamino]-2-benzhydrylquinuclidine (yield, 41%), m.p. 164°–167° C.

Anal. Calcd. for $C_{28}H_{29}F_3N_2$: C, 74.64; H, 6.49; N, 6.22. Found: C, 74.08; H, 6.48; N, 6.06.

EXAMPLE 4

The two-step reaction procedure described in Example 1 was repeated except that 2-methoxybenzylamine was the reagent employed in place of cyclohexylamine, using the same molar proportions as before. In this particular case, the corresponding final product obtained was cis-3-[(2-methoxyphenyl)methylamino]-2-benzhydrylquinuclidine (yield, 71%), m.p. 132°–135° C.

Anal. Calcd. for $C_{28}H_{32}N_2$: C, 81.51; H, 7.82; N, 6.79. Found: C, 81.56; H, 7.86; N, 6.68.

EXAMPLE 5

The two-step reaction procedure described in Example 1 was repeated prepare the following cis-3-[(cyclic)-methylamino]-2-benzhydrylquinuclidines, starting from 3-keto-2-benzhydrylquinuclidine and the appropriate N-(cyclic)methylamine in each instance, and using the same molar proportions as before:

cis-3-[(3-trifluoromethylphenyl)methylamino]-2-benzhydrylquinuclidine, m.p. 197°–199° C.

cis-3-[(4-methoxyphenyl)methylamino]-2-benzhydrylquinuclidine, m.p. 154°–157° C.

cis-3-[(3-pyridyl)methylamino]-2-benzhydrylquinuclidine, m.p. 130°–140° C.

cis-3-[(3,4-dichlorophenyl)methylamino]-2-benzhydrylquinuclidine, m.p. 182°–184° C.

cis-3-[(4-fluorophenyl)methylamino]-2-benzhydrylquinuclidine, m.p. 170°–172° C.

cis-3-[(2-pyridyl)methylamino]-2-benzhydrylquinuclidine, m.p. 95°–115° C.

cis-3-[(4-pyridyl)methylamino]-2-benzhydrylquinuclidine, m.p. 110°–130° C.

cis-3-[(4-chlorophenyl)methylamino]-2-benzhydrylquinuclidine, m.p. 157°–160° C.

cis-3-[(3-methoxyphenyl)methylamino]-2-benzhydrylquinuclidine, m.p. 156°–158° C.

cis-3-[(2,3-dichlorophenyl)methylamino]-2-benzhydrylquinuclidine, m.p. 151°–154° C.

cis-3-[(3-chlorophenyl)methylamino]-2-benzhydrylquinuclidine, m.p. 186°–188° C.

cis-3-[(4-trifluoromethylphenyl)methylamino]-2-benzhydrylquinuclidine, m.p. 171°–173° C.

cis-3-[(2-methylphenyl)methylamino]-2-benzhydrylquinuclidine, m.p. 173°–176° C.

cis-3-[(3-methylphenyl)methylamino]-2-benzhydryl-
   quinuclidine, m.p. 170°–174° C.
cis-3-[(4-methylphenyl)methylamino]-2-benzhydryl-
   quinuclidine, m.p. 175°–178° C.
cis-3-[(3-fluorophenyl)methylamino]-2-benzhydryl-
   quinuclidine, m.p. 156°–159° C.
cis-3-[(4-methoxycarbonylphenyl)methylamino]-2-
   benzhydrylquinuclidine, m.p. 175°–182° C.
cis-3-[(2-fluorophenyl)methylamino]-2-benzhydryl-
   quinuclidine, m.p. 164°–166° C.
cis-3-[(2,5-difluorophenyl)methylamino]-2-benzhydryl-
   quinuclidine, m.p. 163°–165° C.
cis-3-[(2,6-difluorophenyl)methylamino]-2-benzhydryl-
   quinuclidine, m.p. 154°–157° C.
cis-3-[(3-methoxycarbonylphenyl)methylamino]-2-
   benzhydrylquinuclidine, m.p. 182°–185° C.
cis-3-[(3-indolyl)methylamino]-2-benzhydrylquinucli-
   dine, m.p. 207°–212° C.

EXAMPLE 6

A. In a 25 ml. round-bottomed reaction flask equipped with a Dean-Stark trap, reflux condenser and nitrogen-inlet tube, there were placed 505 mg. (0.001405 mole) of 2-[(2,4dichlorophenyl)phenylmethyl]quinuclidin-3-one (the product of Preparation B), 225 mg. (0.002107 mole) of benzylamine, 6.5 mg. (0.000028 mole) of camphorsulfonic acid and 7 ml. of toluene. The reaction mixture was then refluxed azeotropically for a period of 18 hours, cooled to ambient temperatures and concentrated in vacuo to afford a solid residue.

B. The solid residual material obtained above (crude 3-benzylimino)-2-[(2,4-dichlorophenyl)phenylmethyl]-quinuclidine) was next dissolved in 13 ml. of dry tetrahydrofuran, and the resulting solution was cooled to 0° C., with stirring, while under a dry nitrogen atmosphere. At this point, 5.6 ml. (0.002809 mole) of a 0.5M solution of 9-borabicyclononane (9-BBN) in tetrahydrofuran was added to the chilled solution (with stirring), and the resulting reaction mixture was then allowed to warm to room temperature (ca. 20° C.) and thereafter stirred for a period of 24 hours at ambient temperatures. Upon completion of this step, the stirred reaction mixture was next quenched with water, and then partitioned between aqueous 1N hydrochloric acid and methylene chloride, with the organic layer thereafter being separated. The aqueous phase was then adjusted to pH 14 with solid sodium hydroxide and thereafter extracted with fresh methylene chloride. The combined organic extracts were subsequently dried over anhydrous sodium sulfate and filtered, and the resulting filtrate thereafter evaporated to dryness while under reduced pressure to afford a solid residual product. Crystallization of the latter material from isopropanol then gave 154 mg. (24%) of pure cis-3-benzylamino-2-[(2,4-dichlorophenyl)phenylmethyl]quinuclidine as white crystals melting at 142°–147° C. The pure product was further characterized by means of mass spectrum analysis and nuclear magnetic resonance data, in addition to elemental analysis.

Mass Spectrum (%): 451(parent, 0.5), 216(22), 215(72), 96(21), 91(100).

NMR Data: $^1$H-NMR ($\delta$, CDCl$_3$) 1.2–2.1 (series of five multiplets, 5H), 2.7–2.8(m, 4H), 3.1–3.3(m, 2H), 3.6–3.7(m, 2H), 4.84(d, 1H), 6.7–6.8 and 7.1–7.4(m, 8H); $^{13}$C-NMR (CDCl$_3$) 20.1, 24.6, 25.5, 42.1, 44.1, 49.6, 51.9, 53.8, 62.9, 126.4, 126.8, 127.5, 127.9, 128.2, 128.3, 132.3, 139.8, 139.9, 142.6.

Anal. Calcd. for C$_{27}$H$_{28}$Cl$_2$N$_2$: C, 71.84; H, 6.25; N, 6.21. Found: C, 71.04; H, 6.28; N, 5.63.

EXAMPLE 7

The two-step reaction procedure described in Example 6 was repeated except that 2-[(3-methoxyphenyl)-phenylmethyl]quinuclidin-3-one (a product of Preparation C) was the reactant employed in place of 2-[(2,4-dichlorophenyl)phenyl-methyl]quinuclidin-3-one, using the same molar proportions as before. In this particular case, the corresponding final product obtained was cis-3-benzylamino-2-[(3-methoxyphenyl)phenylmethyl]quinuclidine (yield, 33%), m.p. 80°–90° C.

Anal. Calcd. for C$_{28}$H$_{32}$N$_2$O.0.5H$_2$O: C, 79.77; H, 7.89; N, 6.64. Found: C, 79.36; H, 7.78; N, 6.48.

EXAMPLE 8

The two-step reaction procedure described in Example 6 was repeated except that 2-[(4-methoxycarbonylphenyl)phenylmethyl]quinuclidin-3-one (a product of Preparation C) was the reactant employed in place of 2-[(2,4-dichlorophenyl)phenylmethyl]quinuclidin-3-one, using the same molar proportions as before. In this particular case, the corresponding final product obtained was cis-3-benzylamino-2-[(4-methoxycarbonylphenyl)phenylmethyl]quinuclidine (yield, 47%), m.p. 156°–166° C.

Anal. Calcd. for C$_{29}$H$_{32}$N$_2$O$_2$: C, 79.06; H, 7.32; N, 6.36. Found: C, 78.80; H, 7.28; N, 6.28.

EXAMPLE 9

The two-step reaction procedure described in Example 6 was repeated to prepare the following cis-3-benzylamino-2-[($\alpha$-substituted)phenylmethyl]quinuclidines, starting from the corresponding 2-[($\alpha$-substituted)phenylmethyl]quinuclidin-3-one compounds and benzylamine in each instance, and using the same molar proportions as before:

cis-3-benzylamino-2-[(2,3-dichlorophenyl)phenylmethyl]quinuclidine, m.p. 150°–165° C.
cis-3-benzylamino-2-[(2,4-difluorophenyl)phenylmethyl]quinuclidine, m.p. 115°–140° C.
cis-3-benzylamino-2-[(2,3-trifluoromethylphenyl)-phenylmethyl]quinuclidine, m.p. 158°–160° C.
cis-3-benzylamino-2-[(2-furyl)phenylmethyl]quinuclidine, m.p. 135°–143° C.
cis-3-benzylamino-2-[(3,4-dichlorophenyl)phenylmethyl]quinuclidine, m.p. 136°–139° C.
cis-3-benzylamino-2-[(4-pyridyl)phenylmethyl]quinuclidine, m.p. 120°–135° C.
cis-3-benzylamino-2-[(E- and Z-2-tert.-butylvinyl)-phenylmethyl]quinuclidine, m.p. 85°–92° C.
cis-3-benzylamino-2-[(2-methoxyphenyl)phenylmethyl]quinuclidine, m.p. 155°–175° C.
cis-3-benzylamino-2-[(2-n-propyl)phenylmethyl]quinuclidine, m.p. 140°–145° C.
cis-3-benzylamino-2-[(4-carboxyphenyl)phenylmethyl]-quinuclidine, m.p. 180° C. (decomp.)
cis-3-benzylamino-2-[(2-thienyl)phenylmethyl]quinuclidine, m.p. 150°–163° C.
cis-3-benzylamino-2-[(2-biphenyl)phenylmethyl]quinuclidine, m.p. 185°–195° C.

EXAMPLE 10

The procedure described in Example 6 was repeated to prepare the following cis-3-(2-thienyl)amino-2-[($\alpha$-substituted)phenylmethyl] quinuclidines, starting from the corresponding 2-[($\alpha$-substituted)phenylmethyl]- quinuclidin-3-one and 2-thenylamine [which is (2-thienyl)methylamine] in each instance, and using the same molar proportions as before:

cis-3-[(2-thienyl)methylamino]-2-[(2,3-dichlorophenyl)phenylmethyl]quinuclidine, m.p. 129°–142° C.

cis-3-[(2-thienyl)methylamino]-2-[(2,4-dichlorophenyl)phenylmethyl]quinuclidine, m.p. 133°–138° C.

cis-3-[(2-thienyl)methylamino]-2-[(3-methoxyphenyl)phenylmethyl]quinuclidine, m.p. 105°–115° C.

cis-3-[(2-thienyl)methylamino]-2-[(cyclohexyl)phenylmethyl]quinuclidine, m.p. 140°–147° C.

cis-3-[(2-thienyl)methylamino]-2-[(3-pyridyl)phenylmethyl]quinuclidine, m.p. 147°–153° C.

EXAMPLE 11

In a 50 ml. round-bottomed reaction flask equipped with reflux condenser and nitrogen-inlet tube, there were placed 1.022 g. (0.0035 mole) of 3-amino-2-benzhydrylquinuclidine ]prepared according to the procedure described by E. J. Warawa et al. in the *Journal of Medicinal Chemistry*, Vol. 18, p. 71(1975)], 918.7 mg. (0.00525 mole) of 2,6-dichlorobenzaldehyde, 16 mg of camphorsulfonic acid and 18 ml. of toluene. The resulting reaction mixture was next refluxed for a period of 18 hours azeotropically, and then cooled to room temperature (ca. 20° C.) and evaporated to near dryness while under reduced pressure to afford a solid residue. Crystallization of the latter material from isopropanol then gave 1.32 g. (84%) of pure cis-3-[(2,6-dichlorophenyl)methyleneamino]-2-benzhydrylquinuclidine as a white solid, m.p. 178°–182° C.; IR(cm$^{-1}$, KBr), 1642(C=N). The pure product was further characterized by means of mass spectrum analysis, and nuclear magnetic resonance data, in addition to elemental analysis.

Mass Spectrum (%): 427(<1, parent+1), 291(38), 274(21), 260(310, 259)(100), 135(21), 96(21), 91(27).

NMR Data: $^1$H-NMR (δ, CDCl$_3$) 1.45(m, 1H), 1.81(m, 3H), 2.26(m, 1H), 2.89(m, 1H), 3.08(m, 2H, 3.60(m, 1H), 3.71(m, 1H), 4.01(dd, 2H), 4.68(d, 1H), 7.1–7.5(m, 13H), 7.96(2, 1H), $^{13}$C-NMR (CDCl$_3$) 22.0, 25.4, 31.8, 42.4, 49.5, 50.2, 63.1, 71.3, 125.9, 127.8, 128.2, 128.3, 128.4, 129.3, 130.0, 130.8, 135.5, 143.4, 145.4, 155.8.

Anal. Calcd. for C$_{27}$H$_{28}$Cl$_2$N$_2$: C, 72.16; H, 5.83; N, 6.23. Found: C, 71.50; H, 5.79; N, 6.14.

EXAMPLE 12

The procedure described in Example 11 was repeated except that 2-methoxybenzaldehyde was the reagent employed instead of 2,6-dichlorobenzaldehyde, using the same molar proportions as before. In this particular case, the corresponding final product obtained was cis-3-[(2-methoxyphenyl)methyleneamino]-2-benzhydrylquinuclidine (yield, 78%), m.p. 157°–161° C.

Anal. Calcd. for C$_{28}$H$_{30}$N$_2$: C, 81.91; H, 7.36; N, 6.82. Found: C, 81.49; H, 4.76; N, 6.70.

EXAMPLE 13

The procedure described in Example 11 is followed to prepare the following cis-3-(homocyclic)methyleneamino]-2-benzhydrylquinuclidines, starting from 3-amino-2-benzhydrylquinuclidine and the appropriate alicyclic or aromatic aldehyde compound in each instance, and using the same molar proportions as before:

cis-3-[(2-carboxyphenyl)methyleneamino]-2-benzhydrylquinuclidine cis-3-[(cyclopentyl)methyleneamino]-2-benzhydrylquinuclidine cis-3-[(2-biphenyl)methyleneamino]-2-benzhydrylquinuclidine.

EXAMPLE 14

In a 25 ml. round-bottomed reaction flask equipped with reflux condenser and nitrogen-inlet tube, there were placed 401 mg. (0.000894 mole) of cis-3-[(2,6-dichlorophenyl)methyleneamino]-2-benzhydrylquinuclidine (the product of Example 11) in 4 ml. of dry tetrahydrofuran and 2.2 ml. (0.004471 mole) of a 2.0M solution of borane-methyl sulfide in tetrahydrofuran. The reaction mixture was next refluxed for a period of five days, then cooled to room temperature (ca. 20° C.) and evaporated to near dryness while under reduced pressure. The solid residue so obtained was next taken up in 5 ml. of ethanol, treated with 500 mg. of solid sodium carbonate and then refluxed for a period of two days. The reaction solution was then cooled to ambient temperatures and thereafter partitioned between ethyl acetate and water, followed by separation of the two layers. The separated ethyl acetate layer was next extracted with 1N aqueous hydrochloric acid and the resulting aqueous acidic layer was thereafter adjusted to pH 10 with solid sodium hydroxide pellets, followed by extraction with methylene chloride. The organic layer thus obtained was then washed with brine and subsequently dried over anhydrous sodium sulfate. After removal of the drying agent by means of filtration and the solvent by means of evaporation under reduced pressure, there was finally obtained a solid residue which crystallized from isopropanol to afford 124 mg. (31%) of pure cis-3-[(2,6-dichlorophenyl)methylamino]-2-benzhydrylquinuclidine as a white solid material melting at 155°–160° C. The pure product was further characterized by means of mass spectrum analysis and nuclear magnetic resonance data, in addition to elemental analysis.

Mass Spectrum (%): 394(1.4, parent), 289(19), 228(20), 227(100), 158(28), 110(19).

NMR Data: $^1$H-NMR (δ, CDCl$_3$) 1.38(m, 1H), 1.6–1.8(m, 3H), 2.1–2.2(m, 1H), 2.72(m, 1H), 2.88(m, 2H, 3.15(m, 1H), 3.30(m, 1H), 3.57(m, 1H), 3.82(m, 1H), 3.93(m, 1H), 4.51(3, 1H), 7.0–7.5(m, 13H). $^{13}$C-NMR (CDCl$_3$) 20.1, 25.6, 25.7, 42.1, 47.3, 49.0, 49.6, 56.1, 61.9, 125.9, 126.6, 127.5, 127.6, 128.1, 128.4, 128.6, 129.2, 136.0, 136.1, 142.8, 145.8.

Anal. Calcd. for C$_{27}$H$_{28}$Cl$_2$N$_2$.0.5H$_2$O: C, 70.43; H, 6.35; N, 6.08. Found: C, 70.64; H, 6.17; N, 6.08.

EXAMPLE 15

The procedure described in Example 14 was repeated to prepare the following cis-3-[(homocyclic)methylamino-2-benzhydrylquinuclidines, starting from the corresponding cis-3-[(homocyclic)methyleneamino]-2-benzhydrylquinuclidine final products of Example 13 in each instance, and using the same molar proportions as before:

cis-3-[(2-carboxyphenyl)methylamino]-2-benzhydrylquinuclidine, m.p. 238°–241° C.

cis-3-[(cyclopentyl)methylamino]-2-benzhydrylquinuclidine, m.p. 158°–160° C.

cis-3-[(2-biphenyl)methylamino]-2-benzhydrylquinuclidine, m.p. 137°–143° C.

EXAMPLE 16

In a 50 ml. round-bottomed reaction flask equipped with reflux condenser and nitrogen-inlet tube, there were placed 838 mg. (0.002024 mole) of 3-(2-norbornylcarbonylamino)-2-benzhydrylquinuclidine (the product of Preparation D), 10 ml. of dry tetrahydrofuran and 5.06 ml. (0.010119 mole) of a 2.0M solution of borane-methyl sulfide in tetrahydrofuran. The reaction mixture was next refluxed for a period of four days, then cooled to room temperature (ca. 20° C.) and evaporated to near dryness while under reduced pressure. The solid residue so obtained was next taken up in 20 ml. of ethanol, treated with 100 mg. of solid sodium carbonate and then refluxed for a period of 24 hours. The reaction solution was then cooled to ambient temperatures and thereafter partitioned between water and methylene chloride, followed by separation of the two layers. The separated methylene chloride layer was next extracted with 1N aqueous hydrochloric acid, and the resulting aqueous acidic layer was thereafter adjusted to pH 10 with solid sodium hydroxide pellets, followed by extraction again with methylene chloride. The organic layer thus obtained was then washed with brine and subsequently dried over anhydrous sodium sulfate. After removal of the drying agent by means of filtration and the solvent by means of evaporation under reduced pressure, there was finally obtained a solid residue which crystallized from isopropanol to give 474 mg. (58%) of pure cis-3-[(2-norbornyl)methylamino]-2-benzhydrylquinuclidine as a white solid melting at 183°–189° C. The pure product was further characterized by means of mass spectrum analysis and nuclear magnetic resonance data, in addition to elemental analysis.

Mass Spectrum (%): 401(<1.4, parent+1), 234(43), 233(100), 176(21), 164(25), 110(29), 67(29).

NMR Data: $^1$H-NMR ($\delta$, CDCl$_3$) 0.6–3.0(several multiplets, 22H), 3.27(m, 1H), 3.75(dd, 1H), 4.51(dd, 1H), 7.1–7.5(10H). $^{13}$C-NMR (CDCl$_3$) 19.9, 20.1, 20.2, 21.9, 22.9, 25.0, 25.1, 25.2, 25.5, 25.6, 28.9, 30.0, 30.1, 35.4, 36.1, 36.6, 36.8, 37.6, 38.6, 38.7, 38.8, 39.3, 39.7, 39.8, 42.1, 42.2, 49.3, 49.5, 49.6, 49.7, 51.4, 51.5, 55.7, 56.9, 57.1, 61.9, 62.0, 126.0, 126.9, 126.6, 127.4, 127.5, 128.4, 129.2, 143.2, 143.4, 145.4.

Anal. Calcd. for $C_{28}H_{36}N_2 \cdot 0.25H_2O$: C, 83.02; H, 9.08; N, 6.92. Found: C, 82.98; H, 8.91; N, 6.84.

EXAMPLE 17

The procedure described in Example 16 was repeated to prepare the following cis-3-[(homocyclic)methylamino]-2-benzhydrylquinuclidines, starting from the corresponding cis-[(homocyclic)carbonylamino]-2-benzhydrylquinuclidine final products of Preparation E in each instance, and using the same molar proportions as before:

cis-3-[(1-norbornyl)methylamino]-2-benzhydrylquinuclidine, m.p. 173°–179° C.

cis-3-[(2-benzylphenyl)methylamino]-2-benzhydrylquinuclidine, m.p. 119°–121° C.

cis-3-[(3,5-difluorophenyl)methylamino]-2-benzhydrylquinuclidine, m.p. 119°–127° C.

cis-3-[(2,3-difluorophenyl)methylamino]-2-benzhydrylquinuclidine, m.p. 148°–157° C.

EXAMPLE 18

The first part and only this part of the two-step reaction procedure described in Example 1 (i.e., the condensation step) is repeated to prepare the following 3-[(cyclic)methylimino]-2-benzhydrylquinuclidines, starting from 3-keto-2-benzhydryl-quinuclidine and the appropriate N-(cyclic)methylamine in each instance, and using the same molar proportions as before, except that this time the desired intermediate product is isolated and purified as such via trituration with isopropanol followed by recrystallization from the same solvent to afford the pure imino compound:

3-(cyclohexylmethylimino)-2-benzhydrylquinuclidine

3-[(2-chlorophenyl)methylimino]-2-benzhydrylquinuclidine

3-[(2-trifluoromethylphenyl)methylimino]-2-benzhydrylquinuclidine

3-[(2-methoxyphenyl)methylimino]-2-benzhydrylquinuclidine

3-[(3-trifluoromethylphenyl)methylimino]-2-benzhydrylquinuclidine

3-[(4-methoxyphenyl)methylimino]-2-benzhydrylquinuclidine

3-[(3-pyridyl)methylimino]-2-benzhydrylquinuclidine

3-[(3,4-dichlorophenyl)methylimino]-2-benzhydrylquinuclidine

3-[(4-fluorophenyl)methylimino]-2-benzhydrylquinuclidine

3-[(2-pyridyl)methylimino]-2-benzhydrylquinuclidine

3-[(4-pyridyl)methylimino]-2-benzhydrylquinuclidine

3-[(4-chlorophenyl)methylimino]-2-benzhydrylquinuclidine

3-[(3-methoxyphenyl)methylimino]-2-benzhydrylquinuclidine

3-[(2,3-dichlorophenyl)methylimino]-2-benzhydrylquinuclidine

3-[(3-chlorophenyl)methylimino]-2-benzhydrylquinuclidine

3-[(4-trifluoromethylphenyl)methylimino]-2-benzhydrylquinuclidine

3-[(2-methylphenyl)methylimino]-2-benzhydrylquinuclidine

3-[(3-methylphenyl)methylimino]-2-benzhydrylquinuclidine

3-[(4-methylphenyl)methylimino]-2-benzhydrylquinuclidine

3-[(3-fluorophenyl)methylimino]-2-benzhydrylquinuclidine

3-[(4-carbomethoxyphenyl)methylimino]-2-benzhydrylquinuclidine

3-[(2-fluorophenyl)methylimino]-2-benzhydrylquinuclidine

3-[(2,5-difluorophenyl)methylimino]-2-benzhydrylquinuclidine

3-[(2,6-difluorophenyl)methylimino]-2-benzhydrylquinuclidine

3-[(3-methoxycarbonylphenyl)methylimino]-2-benzhydrylquinuclidine

3-[(3-indolyl)methylimino]-2-benzhydrylquinuclidine

3-[(2-norbornyl)methylimino]-2-benzhydrylquinuclidine

3-[(1-norbornyl)methylimino]-2-benzhydrylquinuclidine

3-[(2-benzylphenyl)methylimino]-2-benzhydrylquinuclidine

3-[(3,5-difluorophenyl)methylimino]-2-benzhydrylquinuclidine

3-[(2,3-difluorophenyl)methylimino]-2-benzhydrylquinuclidine

EXAMPLE 19

The first part and only this part of the two-step reaction procedure described in Example 6 (i.e., the condensation step) is repeated to prepare the following 3-benzylimino-2-[(α-substituted)phenylmethyl]quinuclidines, starting from the corresponding 2-[(α-substituted)-phenylmethyl]quinuclidin-3-one compounds (products of Preparations B–C) and benzylamine in each instance, and using the same molar proportions as before, except that this time the desired intermediate product is isolated and purified as such via trituration with isopropanol followed by recrystallization from the same solvent to afford the pure imino compound:

3-benzylimino-2[(2,4-dichlorophenyl)phenylmethyl]-quinuclidine
3-benzylimino-2[(3-methoxyphenyl)phenylmethyl]-quinuclidine
3-benzylimino-2[(4-methoxycarbonylphenyl)phenylmethyl]quinuclidine
3-benzylimino-2[(2,3-dichlorophenyl)phenylmethyl]-quinuclidine
3-benzylimino-2[(2,4-difluorophenyl)phenylmethyl]-quinuclidine
3-benzylimino-2[(3-trifluoromethylphenyl)phenylmethyl]quinuclidine
3-benzylimino-2[(2-furyl)phenylmethyl]quinuclidine
3-benzylimino-2[(3,4-dichlorophenyl)phenylmethyl]-quinuclidine
3-benzylimino-2[(4-pyridyl)phenylmethyl]quinuclidine
3-benzylimino-2[(E- and Z-2-tert.-butylvinyl)phenylmethyl]quinuclidine
3-benzylimino-2[(2-methoxyphenyl)phenylmethyl]-quinuclidine
3-benzylimino-2[(2-n-propyl)phenylmethyl]quinuclidine
3-benzylimino-2[(4-carboxyphenyl)phenylmethyl]-quinuclidine
3-benzylimino-2[(2-thienyl)phenylmethyl]quinuclidine
3-benzylimino-2[(2-biphenyl)phenylmethyl]quinuclidine

EXAMPLE 20

The procedure described in Example 6 is repeated to prepare the following 3-[(2-thienyl)methylimino]-2-[(α-substituted)phenylmethyl]quinuclidines, starting from the corresponding 2-[(α-substituted)phenylmethyl]quinuclidin-3-one and (2-thienyl)methylamine (i.e., 2-thenylamine) in each instance, and using the same molar proportions as before except that this time the desired intermediate product is isolated as such via trituration with isopropanol followed by recrystallization from the same solvent to afford the pure imino compound:

3-[(2-thienyl)methylimino]-2-[(2,3-dichlorophenyl)-phenylmethyl]quinuclidine
3-[(2-thienyl)methylimino]-2-[(2,4-dichlorophenyl)-phenylmethyl]quinuclidine
3-[(2-thienyl)methylimino]-2-[(3-methoxyphenyl)-phenylmethyl]quinuclidine
3-[(2-thienyl)methylimino]-2-[(cyclohexyl)phenylmethyl]quinuclidine
3-[(2-thienyl)methylimino]-2-[(3-pyridyl)phenylmethyl]quinuclidine

EXAMPLE 21

The procedure described in Example 11 is followed to prepare the following cis-3-[(cyclic)methyleneamino]-2-benzhydrylquinuclidines, starting from 3-amino-2-benzhydrylquinuclidine and the appropriate cyclic aldehyde compound in each instance, and using the same molar proportions as before:

cis-3-(cyclohexylmethyleneamino)-2-benzhydrylquinuclidine
cis-3-[(2-chlorophenyl)methyleneamino]-2-benzhydrylquinuclidine
cis-3-[(2-trifluoromethylphenyl)methyleneamino]-3-benzhydrylquinuclidine
cis-3-[(3-trifluoromethylphenyl)methyleneamino]-2-benzhydrylquinuclidine
cis-3-[(4-methoxyphenyl)methyleneamino]-2-benzhydrylquinuclidine
cis-3-[(3-pyridyl)methyleneamino]-2-benzhydrylquinuclidine
cis-3-[(3,4-dichlorophenyl)methyleneamino]-2-benzhydrylquinuclidine
cis-3-[(4-fluorophenyl)methyleneamino]-2-benzhydrylquinuclidine
cis-3-[(2-pyridyl)methyleneamino]-2-benzhydrylquinuclidine
cis-3-[(4-pyridyl)methyleneamino]-2-benzhydrylquinuclidine
cis-3-[(4-chlorophenyl)methyleneamino]-2-benzhydrylquinuclidine
cis-3-[(3-methoxyphenyl)methyleneamino]-2-benzhydrylquinuclidine
cis-3-[(2,3-dichlorophenyl)methyleneamino]-2-benzhydrylquinuclidine
cis-3-[(3-chlorophenyl)methyleneamino]-2-benzhydrylquinuclidine
cis-3-[(4-trifluoromethylphenyl)methyleneamino]-2-benzhydrylquinuclidine
cis-3-[(2-methylphenyl)methyleneamino]-2-benzhydrylquinuclidine
cis-3-[(3-methylphenyl)methyleneamino]-2-benzhydrylquinuclidine
cis-3-[(4-methylphenyl)methyleneamino]-2-benzhydrylquinuclidine
cis-3-[(3-fluorophenyl)methyleneamino]-2-benzhydrylquinuclidine
cis-3-[(4-methoxycarbonylphenyl)methyleneamino]-2-benzhydrylquinuclidine
cis-3-[(2-fluorophenyl)methyleneamino]-2-benzhydrylquinuclidine
cis-3-[(2,5-difluorophenyl)methyleneamino]-2-benzhydrylquinuclidine
cis-3-[(2,6-difluorophenyl)methyleneamino]-2-benzhydrylquinuclidine
cis-3-[(3-methoxycarbonylphenyl)methyleneamino]-2-benzhydrylquinuclidine
cis-3-[(3-indolyl)methyleneamino]-2-benzhydrylquinuclidine
cis-3-[(2-norbornyl)methyleneamino]-2-benzhydrylquinuclidine
cis-3-[(1-norbornyl)methyleneamino]-2-benzhydrylquinuclidine
cis-3-[(2-benzylphenyl)methyleneamino]-2-benzhydrylquinuclidine
cis-3-[(3,5-difluorophenyl)methyleneamino]-2-benzhydrylquinuclidine
cis-3-[(2,3-difluorophenyl)methyleneamino]-2-benzhydrylquinuclidine

EXAMPLE 22

The quinuclidine compounds of the present invention are tested for substance P antagonist activity in bovine caudate tissue, using a modification of the standard assay procedure described by M. A. Cascieri et al., as reported in the *Journal of Biological Chemistry*, Vol. 258, p. 5158 (1983).

In this procedure, bovine caudate tissue is removed from a −70° C. freezer and homogenized in 50 volumes (w./v.) of ice-cold 50 mM Tris (i.e., tromethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 40 μg./ml. of bacitracin, 4 μg./ml. of leupeptin, 2 μg. of chymostatin and 200 μg./ml. of bovine serum albumin. This step completes the production of the tissue preparation.

The radioligand binding procedure is then carried out in the following manner, viz., by initiating the reaction via the addition of 100 μl. of the test compound made up to a concentration of 1 82 M, followed by the addition of 100 μl. of radioactive ligand made up to a final concentration of 0.5 mM and then finally by the addition of 800 μl. of the tissue preparation produced as described above. The final volume is thus 1.0 ml., and the reaction mixture is next vortexed and incubated at room temperature (ca. 20° C.) for a period of 20 minutes. The tubes are then filtered using a cell harvester, and the glass fiber filters are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

EXAMPLE 23

The following cis-[(cyclic)methylamino]-2-benzhydrylquinuclidine final products of Examples 2, 3 and 4, respectively, were tested for anti-inflammatory activity in rats, using the standard rat foot edema test, according to the general procedure described by C. A. Winter et al., as first reported in the *Proceedings of the Society for Experimental Biology and Medicine*, Vol. 111, p. 544 (1962). The compounds were administered orally (by gavage) at 32 mg./kg. and the results obtained are reported below in terms of the percent (%) inhibition of edema formation afforded by each test compound as compared to the control (i.e., vehicle alone with no compound):

| Compound | % Inhibition at 32 mg./kg. |
| --- | --- |
| Product of Example 2 | 29 |
| Product of Example 3 | 50 |
| Product of Example 4 | 38 |

EXAMPLE 24

The two-step reaction procedure described in Example I was repeated except that 3,4-dimethoxybenzylamine was the reagent employed in place of cyclohexylamine, using the same molar proportions as before. In this particular case, the corresponding final product obtained was cis-3-[(3,4-dimethoxyphenyl)methylamino]-2-benzhydrylquinuclidine as a quarter hydrate, m.p. 120°–123° C.

Anal. Calcd. for $C_{29}H_{34}N_2O_2 \cdot 0.25H_2O$: C, 77.91; H, 7.78; N, 6.27. Found: C, 78.07; H, 7.65; N, 6.30.

EXAMPLE 25

The two-step reaction procedure described in Example 6 was repeated to prepare the following cis-3-[(cyclic)methylamino]-2-[(α-substituted)arylmethyl]quinuclidines (characterized, in some instances, as the hydrochloride salt), starting from the corresponding 2-[(α-substituted)arylmethyl]quinuclidin-3-one compounds and the appropriate N-(cyclic)methylamine in each instance, and using the same molar proportions as before:

cis-3-benzylamino-2-[(2-benzylphenyl)phenylmethyl]quinuclidine dihydrochloride 1.5 hydrate, m.p. 175°–180° C.

cis-3-[(2-methoxyphenyl)methylamino]-2-[(2-thienyl)phenylmethyl]quinuclidine, m.p. 130°–140° C.

cis-3-[(2-methoxyphenyl)methylamino]-2-[(3methoxyphenyl)phenylmethyl]quinuclidine dihydrochloride 1.5 hydrate, m.p. 170°–177° C.

cis-3-[(2-methoxyphenyl)methylamino]-2-[(2,4-difluorophenyl)phenylmethyl]quinuclidine semihydrate, m.p. 115°–131° C.

cis-3-[(2-methoxyphenyl)methylamino]-2-[(2-furyl)phenylmethyl]quinuclidine, m.p. 105°–110° C.

cis-3-[(2-methoxyphenyl)methylamino]-2-[(2,3-dichlorophenyl)phenylmethyl]quinuclidine. 0.25 hydrate, m.p. 132°–136° C.

cis-3-[(2-methoxyphenyl)methylamino]-2-[(2,4-dichlorophenyl)phenylmethyl]quinuclidine, 0.25 hydrate, m.p. 135°–138° C.

cis-3-[(2-methoxyphenyl)methylamino]-2-[(3,4-difluorophenyl)phenylmethyl]quinuclidine semihydrate, m.p. 115°–118° C.

cis-3-[(2-methoxyphenyl)methylamino]-2-[(3-pyridyl)phenylmethyl]quinuclidine dihydrochloride 3.5 hydrate, m.p. 170°–190° C.

cis-3-[(2-methoxyphenyl)methylamino]-2-[(2-methoxyphenyl)phenylmethyl]quinuclidine semihydrate, m.p. 150°–155° C.

cis-3-[(2-methoxyphenyl)methylamino]-2-[(3-trifluoromethylphenyl)phenylmethyl]quinuclidine trihydrate, m.p. 190°–200° C.

cis-3-benzylamino-2-[(2-benzylphenyl)phenylmethylquinuclidine hydrochloride, m.p. 175°–180° C.

cis-3-benzylamino-2-[(2-thienyl)phenylmethyl]quinuclidine m.p. 165°–175° C.

cis-3-[(2-methoxyphenyl)methylamino]-2-[(3-thienyl)phenylmethyl]quinuclidine semihydrate, m.p. 145°–153° C.

cis-3-[(2-methoxyphenyl)methylamino]-2-[bis-(2-thienyl)methylquinuclidine 0.25 hydrate, m.p. 135°–140° C.

cis-3-benzylamino-2-]bis-(2-thienyl)methyl]quinuclidine, m.p. 147°–150° C.

cis-3-benzylamino-2-](2-thienyl,3-thienyl)methyl]quinuclidine, m.p. 152°–160° C.

cis-3-[(2-methylphenyl)methylamino]-2-[(2-thienyl,3-thienyl)methyl]quinuclidine, m.p. 115°–125° C.

cis-3-benzylamino-2-[(2-fluorophenyl)methyl]quinuclidine 0.25 hydrate, m.p. 144°–150° C.

cis-3-[2-methoxyphenyl)methylamino]-2-[(2-fluorophenyl)methyl]quinuclidine, m.p. 156°–164° C.

cis-3-benzylamino-2-[bis(4-fluorophenyl)methyl]quinuclidine, m.p. 148°–152° C.

cis-3-benzylamino-2-[bis(4-bromophenyl)methyl]quinuclidine semihydrate, m.p. 198°–200° C.

cis-3-[(2-methoxyphenyl)methylamino]-2-[bis(4-bromophenyl)methyl]quinuclidine, m.p. 166°-169° C.
cis-3-[(3,4-dimethoxyphenyl)methylamino]-2-[bis(4-bromophenyl)methyl]quinuclidine, m.p. 173°-177° C.
cis-3-benzylamino-2-[bis(3-thienyl)methyl]quinuclidine, m.p. 168°-173° C.
cis-3-[(2-methoxyphenyl)methylamino]-2-[bis(4-thienyl)methyl]quinuclidine semihydrate, m.p. 135°-138° C.
cis-3-benzylamino-2-[bis(3-fluorophenyl)methyl]quinuclidine, m.p. 132°-136° C.
cis-3-[(2-methoxyphenyl)methylamino]-2-[bis(3-fluorophenyl)methyl]quinuclidine, m.p. 125°-129° C.
cis-3-benzylamino-2-[(2-fluorophenyl)methyl]quinuclidine, m.p. 139°-144° C.
cis-3-[(2-methoxyphenyl)methylamino]-2-[(2-fluorophenyl-3-fluorophenyl)methyl]quinuclidine, m.p. 127°-131° C.

EXAMPLE 26

The procedure described in Example 11 was repeated except that 2-allyloxybenzaldehyde was the reagent employed instead of 2,6-dichlorobenzaldehyde, using the same molar proportions as before. In this particular case, the corresponding final product obtained was cis-3-[(2-allyloxyphenyl)methyleneamino]-2-benzhydrylquinuclidine, m.p. 155°-162° C.

Anal. Calcd. for $C_{30}H_{32}N_2O$: C, 82.53; H, 7.39; N, 6.42. Found: C, 82.03; H, 7.48; N, 6.21.

EXAMPLE 27

In a 50 ml. round-bottomed reaction flask equipped with a nitrogen-inlet tube, there were placed 615 mg. (0.0011412 mole) of cis-3-](2-allyloxyphenyl)methyleneamino]-2-benzhydrylquinuclidine (the product of Example 26), 7.0 ml. of trifluoroacetic acid and 0.70 ml. (0.004235 mole) of triethylsilane. The reaction mixture was next stirred at room temperature (ca. 20° C.) for a period of three days, and thereafter poured into 1N aqueous hydrochloric acid and washed with methylene chloride. After adjusting the pH of the separated aqueous layer to pH 9.0 with solid sodium carbonate, followed by extraction with fresh methylene chloride, the organic layers were combined and subsequently dried over anhydrous sodium sulfate. After removal of the drying agent by means of filtration and the solvent by means of evaporation under reduced pressure, there was ultimately obtained a solid residue which crystallized from isopropanol to afford 275 mg. (45%) of pure cis-3-[(2-allyloxyphenyl)methylamino]-2-benzhydrylquinuclidine as the quarter hydrate in the form of a white solid melting at 117°-120° C.

Anal. Calcd. for $C_{30}H_{34}N_2O.0.25\ H_2O$: C, 81.32; H, 7.85; N, 6.32. Found: C, 81.38; H, 7.72; N, 6.35.

EXAMPLE 28

A. The reaction procedure described in Example 11 was repeated except that 2-(methoxycarbonylmethoxy)benzaldehyde was the reagent employed instead of 2,6-dichlorobenzaldehyde, using the same molar proportions as before. In this particular case, the corresponding final product obtained was cis-3-{[2-(methoxycarbonylmethoxy)phenyl]methyleneamino}-2-benzhydrylquinuclidine.

B. In a 100 ml. round-bottomed reaction flask equipped with a nitrogen-inlet tube, there were placed 5.47 g. (0.01168) mole) of the above methyleneamine, 4.06 g. (0.03504 mole) of triethylsilane, 29 ml. of trifluoroacetic acid and 0.4 ml. of methanesulfonic acid. The reaction mixture was next stirred at room temperature (ca. 20° C.) for a period of seven days, and thereafter poured into a mixture of methylene chloride and aqueous sodium bicarbonate. The two layers were then separated, and the organic layer was washed with 6N aqueous hydrochloric acid. The resulting aqueous acidic layer was then separated and neutralized with 6N aqueous sodium hydroxide, followed by extraction with fresh methylene chloride. The organic layers were then combined and subsequently dried over anhydrous sodium sulfate. After removal of the drying agent by means of filtration and the solvent by means of evaporation under reduced pressure, there was finally obtained a solid residue that was thereafter treated with 30 ml. of methanol and 3.0 ml. of 6N aqueous hydrochloric acid. The latter mixture was next stirred and heated for a period of four hours, followed by a work-up which first involved basification and then organic solvent extraction with methylene chloride. Evaporation of the latter solution under reduced pressure finally gave a solid residue, which thereafter crystallized from isopropanol (in two crops) to ultimately afford 140 mg. (2.5%) of pure cis-3-[2-(methoxycarbonylmethoxy)phenyl]methylamine-2-benzhydrylquinuclidine 0.75 hydrate in the form of a white solid melting at 114°-117° C.

Anal. Calcd. for $C_{30}H_{34}N_2O_3.0.75H_2O$: C, 74.43; H, 7.39; N, 5.79. Found: C, 74.46; H, 7.09; N, 5.82.

EXAMPLE 29

The condensation and reduction reaction procedures (two-steps) described in Examples 11 and 14, respectively, were repeated to prepare the following cis-3[(cyclic)methylamino]-2-benzhydrylquinuclidines (characterized, in some instances, as the hydrochloride salt), starting from 3-amino-2-benzhydrylquinuclidine and the appropriate cyclic aldehyde of choice and proceeding through the corresponding cis-[(cyclic)methylamino]-2-benzhydrylquinuclidine intermediate in each instance, using the same molar proportions as before in each step:

cis-3-[(2,3-dimethoxyphenyl)methylamino]-2-benzhydrylquinuclidine 0.25 hydrate, m.p. 158°-162° C.
cis-3-[(2,4-dimethoxyphenyl)methylamino]-2-benzhydrylquinuclidine 0.25 semihydrate, m.p. 120°-125° C.
cis-3-[(2,5-dimethoxyphenyl)methylamino]-2-benzhydrylquinuclidine 0.25 semihydrate, m.p. 120°-122° C.
cis-3-[(2-hydroxyphenyl)methylamino]-2-benzhydrylquinuclidine 1.25 hydrate, m.p. 169°-175° C.
cis-3-[(2-ethoxyphenyl)methylamino]-2-benzhydrylquinuclidine hydrate, m.p. 159°-166° C.
cis-3-[(2-ethoxy-3-methoxyphenyl)methylamino]-2-benzhydrylquinuclidine 1.25 hydrate, m.p. 128°-138° C.
cis-3-[(2-hydroxy-3-methoxyphenyl)methylamino]-2-benzhydrylquinuclidine dihydrochloride dihydrate, m.p. 170°-190° C.
cis-3-[(2-hydroxy-2-methoxyphenyl)methylamino]-2-benzhydrylquinuclidine dihydrochloride dihydrate, m.p. 180°-200° C.
cis-3-[(2-methoxynaphth-1-yl-methylamino]-2-benzhydrylquinuclidine dihydrochloride 2.2 hydrate, m.p. 210°-230° C.
cis-3-[(5-chloro-2-methoxyphenyl)methylamino]-2-benzhydrylquinuclidine semihydrate, m.p. 183°-188° C.
cis-3-[(2-hydroxyethoxy)phenyl)methylamino]-2-benzhydrylquinuclidine, m.p. 136°-139° C.

cis-3-[(5-hydroxymethyl-2-methoxyphenyl)methylamino]-2-benzhydrylquinuclidine semihydrate, m.p. 155°-160° C.
cis-3-[(2-methoxynaphth-1-yl)methylamino]-2-benzhydrylquinuclidine 0.25 hydrate, m.p. 156°-163° C.
cis-3-[(3-methoxythien-2-yl)methylamino]-2-benzhydrylquinuclidine, m.p. 130°-135° C.
cis-3-[(3,5-dimethoxyphenyl)methylamino]-2-benzhydrylquinuclidine 0.25 hydrate, m.p. 154°-157° C.
cis-3-[(quinol-8-yl)methylamino]-2-benzhydrylquinuclidine hydrochloride 3.75 hydrate, m.p. 245°-255° C.
cis-3-[(2,3-dihydrobenzofur-7-yl)methyl]-2-benzhydrylquinuclidine, m.p. 148°-151° C.
cis-3-[(2,6-dimethylphenyl)methylamino]-2-benzhydrylquinuclidine, m.p. 156°-159° C.
cis-3-[(2,3-methylenedioxyphenyl)methylamino]-2-benzhydrylquinuclidine, m.p. 161°-164° C.
cis-3-[(2-methoxyphenyl)methylamino]-2-benzhydrylquinuclidine, m.p. 154°-155° C.; $[\alpha]_D^{20°} - 23.8°$-(c=1, methylene chloride) at 589 nM.

EXAMPLE 30

The reaction procedures (two-steps) described in Examples 11 and 14, respectively, were repeated except that 6-hydroxy-2-methoxybenzaldehyde was the starting material employed in place of 2,6-dichlorobenzaldehyde in the first step (see Example 14), using the same molar proportions as before in each step. In this particular case, the corresponding final product obtained (after first proceeding via the corresponding methyleneamino intermediate) was cis-3-[(6-hydroxy-2-methoxyphenyl)methylamino]-2-benzhydrylquinuclidine as a quarter hydrate, m.p. 176°-180° C.

Anal. Calcd. for $C_{28}H_{32}N_2O_2 \cdot 0.25H_2O$: C, 77.66; H, 7.56; N, 6.47. Found: C, 77.24; H, 7.47; N, 6.29.

EXAMPLE 31

The reaction procedures (two-steps) described in Examples 11 and 27, respectively, were repeated except that 2-methoxy-5-nitrobenzaldehyde was the reagent employed in place of of 2,6-dichlorobenzaldehyde in the first step (see Example 11), using the same molar proportions as before, to readily afford cis-3-[(2-methoxy-5-nitrophenyl)methylamino]-2-benzhydrylquinuclidine as the desired intermediate product; and the latter was then the starting material employed in the second step (see Examples 27), again using the same molar proportions as before, to ultimately yield cis-3-[(2-methoxy-2-nitrophenyl)methylamino]-2-benzhydrylquinuclidine semihydrate (m.p. 212°-215° C.) as the corresponding final product.

Anal. Calcd. for $C_{28}H_{31}N_3O_3 \cdot 0.5H_2O$: C, 72.08; H, 6.91; N, 9.01. Found: C, 72.15; H, 6.71; N, 9.21.

EXAMPLE 32

The procedure described in Example 16 was repeated to prepare the following cis-3-[(cyclic)methylamino]-2-benzhydrylquinuclidines, starting from the corresponding cis-3-[(cyclic)carbonylamino]-2-benzhydrylquinuclidine compound in each instance, and using the same molar proportions as before:
cis-3-[(3-hydroxy-2-pyridyl)methylamino]-2-benzhydrylquinuclidine 1.75 hydrate, m.p. 175°-190° C.
cis-3-[(2-ethylphenyl)methylamino]-2-benzhydrylquinuclidine 0.25 hydrate, m.p. 145°-150° C.
cis-3-[(2-methoxy-5-trifluoromethylphenyl)methylamino]-2-benzhydrylquinuclidine 0.25 hydrate, m.p. 137°-140° C.
cis-3-[(5-fluoro-2-methoxyphenyl)methylamino]-2-benzhydrylquinuclidine, m.p. 164°-167° C.
cis-3-[(3-fluoro-2-methoxyphenyl)methylamino]-2-benzhydrylquinuclidine, m.p. 159°-162° C.
cis-3-{[(2-(N-monomethylamino)phenyl]methylamino}-]-2-benzhydrylquinuclidine 0.75 hydrate, m.p. 173°-176° C.

EXAMPLE 33

A. In a 125 ml. round-bottomed reaction flask equipped with reflux condenser and nitrogen-inlet tube, there was placed a solution consisting of 2.28 g. (0.00507 mole) of cis-3-amino-2-[bis(4-bromophenyl)methyl]-quinuclidine (prepared according to the method described by E. J. Warawa et al. in U.S. Pat. No. 3,560,510) and 1.0 g. (0.00507 mole) of S-(+)-(1-naphthyl)ethyl isocyanate all dissolved in 40 ml. of toluene. The solution was then refluxed for a period of four hours and filtered while hot to recover the insoluble white precipitate that had formed during the course of the reflux reaction step. The solid product so obtained was then washed with toluene and subsequently air-dried to constant weight to afford 1.17 g. (36%) of pure (+)-cis-[(1-naphthylethylureido]-2-[bis(4-bromophenyl)methyl]quinuclidine as the 1.5 hydrate, m.p. 284°-285° C.; $[\alpha]_D^{20°} + 62.0°$(c=1.0, dimethylsulfoxide) at 589 nm.

Anal. Calcd. for $C_{33}H_{33}Br_2N_3O$: C, 61.22; H, 5.14; N, 6.49. Found: C, 60.96; H, 5.14; N, 6.43.

B. In a 125 ml. round-bottomed reaction flask equipped with reflux condenser and nitrogen-inlet tube, there were placed 1.10 g. (0.0017 mole) of the intermediate obtained above and 4.0 ml. of water. To the resulting stirred aqueous mixture, there were then carefully added 8.0 ml. of concentrated sulfuric acid, followed by gentle refluxing (bath temperature, ca. 160° C.) for a period of 22 hours. The resulting dark reaction mixture was then cooled to room temperature (ca. 20° C.), poured into ice and the pH of the chilled aqueous mixture subsequently adjusted to pH 12 with 6N aqueous sodium hydroxide solution. The basified aqueous mixture was next extracted twice with methylene chloride, and the saved organic layers subsequently dried over anhydrous sodium sulfate and filtered. After removal of the drying agent by means of filtration and the solvent by means of evaporation under reduced pressure, the residual material was subsequently chromatographed on a silica gel column, using a 2:1 (by volume) methylene chloride/methanol solvent mixture as the eluent to afford a crude oil as the product. Decolorization of the latter material with charcoal in hot ethyl acetate then gave 643 mg. (84%) of pure (−)-cis-3-amino-2-[bis(4-bromophenyl)methyl]quinuclidine in the form of a white solid product, m.p. 185°-187° C.; $[\alpha]_D^{20°} - 38.8°$ (c=1.0, methylene chloride) at 589 nm.

Anal. Calcd. for $C_{20}H_{22}Br_2N_2$: C, 53.36; H, 4.93; N, 6.22. Found: C, 53.16; H, 4.99; N, 6.16.

C. In a 100 ml round-bottomed reaction flask equipped with a Dean-Stark trap, reflux condenser and nitrogen-inlet tube, there were placed 270 mg. (0.0006 mole) of (−)-cis-3-amino-2-[bis(4-bromophenyl)methyl]quinuclidine (obtained as above), 122 mg. (0.0009 mole) of 2-methoxybenzaldehyde, 2.0 mg. of camphorsulfonic acid and 17 ml. of toluene. The resulting reaction mixture was next refluxed for a period of 24 hours, and then cooled to room temperature (ca. 20° C.) and evaporated to near dryness while under reduced pressure to afford a solid residue which consisted essentially of crude (−)-cis-3-[(2-methoxyphenyl)methyleneamino]-2-[bis(4-bromophenyl)methyl]quinuclidine.

D. The above methyleneamine intermediate (obtained as above) was then taken up in 3.0 ml. of tetrahydrofuran and the resulting ethereal mixture was treated with 1.5 ml. (0.003 mole) of a 2.0M solution of borane-methyl sulfide. The reaction mixture was next refluxed for a period of 24 hours, then cooled to room temperature (ca. 20° C.) and evaporated to near dryness while under reduced pressure. The solid residue so obtained was next taken up in 20 ml. of ethanol, treated with 500 mg. of solid sodium carbonate and 500 mg. of cesium fluoride, and then refluxed for a period of 3.5 days. The resulting reaction mixture was then cooled to ambient temperatures, evaporated to near dryness while under reduced pressure and thereafter partitioned between ethyl acetate and water, followed by the separation of the two layers. The separated organic layer was next washed with aqueous sodium bicarbonate solution and then with brine, and thereafter dried over anhydrous sodium sulfate. After removal of the drying agent by means of filtration and the solvent by means of evaporation under reduced pressure, there was finally obtained a solid product as the residue. The latter material was subsequently chromatographed on silica gel, using a 7.3 (by volume) methylene chloride/methanol solvent mixture as the eluent to ultimately afford on trituration with isopropanol 226 mg. (66%) of pure(−)-cis-3-[(2-methoxyphenyl)methylamino]-2-[bis(4-bromophenyl)methyl]quinuclidine in the form of a white solid product, m.p. 176°-177.5° C.; $[\alpha]_D^{20°} -23.7°(c=1.5$, methylene chloride) at 589 nm.

Anal. Calcd. for $C_{28}H_{30}Br_2N_2O$: C, 58.96; H, 5.30; N, 4.91. Found: C, 58.62; H, 5.06; N, 4.97.

EXAMPLE 34

In a 20 ml. round-bottomed reaction flask equipped with reflux condenser and nitrogen-inlet tube, there was placed 200 mg. (0.000438 mole) of cis-[2-methoxy-5-nitrophenyl)methylamino]-2-benzhydrylquinuclidine (the product of Example 31) in 1.0 ml. of ethanol containing 138 mg. (0.002188 mole) of ammonium formate and 80 mg. of 10% palladium-on-carbon catalyst. The reaction mixture was then stirred at room temperature (ca. 20° C.) for a period of 45 minutes, filtered through Celite (siliceous earth), and the resulting filtrate thereafter evaporated to near dryness while under reduced pressure. The solid residue thus obtained was then crystallized from isopropanol to afford 86 mg. (46%) of pure cis-3-[(5-amino-2-methoxyphenyl)methylamino]-2-benzhydrylquinuclidine, m.p. 164°-169° C.

Anal. Calcd. for $C_{283}H_{33}N_3O$: C, 78.65; H, 7.78; N, 9.83. Found: C, 78.73; H, 7.87; N, 9.71.

EXAMPLE 35

In a 65 ml. round-bottomed reaction flask equipped with nitrogen-inlet tube, there was placed 730 mg. (0.0025 mole) of cis-3-amino-2-benzhydrylquinuclidine [E. J. Warawa et al. in the *Journal of Medicinal Chemistry*, Vol. 18, p. 71(1975)] in 12 ml. of methanol containing 1.0 ml. of a 2.5M solution of hydrochloric acid in methanol. Stirring was commenced and as soon as complete solution was obtained, there was added 810 mg. (0.00375 mole) of 5-bromo-2-methoxybenzaldehyde to the mixture, followed by further stirring until solution was once again achieved. To the resulting stirred solution, there was then added 320 mg (0.0050 mole) of sodium cyanoborohydride and the resulting reaction mixture stirred at room temperature (ca. 20° C.) for a period of 16 hours. The precipitate thus obtained was then recovered from the reaction mixture by means of suction filtration, washed with methanol and subsequently dried in vacuo to constant weight to give 715 mg. (58%) of pure cis-3-[(5-bromo-2-methoxyphenyl)methylamino]-2-benzylhydrylquinuclidine semihydrate, m.p. 190°-191° C.

Anal. Calcd. for $C_{28}H_{31}BrN_2O$ 0.5$H_2O$: C, 67.20; H, 6.44; N, 5.60. Found: C, 67.16; H, 6.13; N, 5.66.

EXAMPLE 36

The procedure described in Example 35 was repeated except that 2-(carboxymethoxy)benzaldehyde was the reagent employed instead of 5-bromo-2-methoxybenzaldehyde, using the same molar proportions as before. In this particular case, the corresponding final product obtained was cis-3-{[2-(carboxymethoxy)phenyl]methylamino}-2-benzhydrylquinuclidine, m.p. 132°-137° C. The yield of pure product amounted to 70% of the theoretical value.

EXAMPLE 37

The two-step reaction procedure described in Example 6 was repeated except that 2-benzhydryl-5-ethylquinuclidine-3-one (a product of Preparation C) and 2-methoxybenzylamine were the initial starting materials employed in place of 2-[(2,4-dichlorophenyl)phenylmethyl]quinuclidine-3-one and benzylamine, using the same molar proportions as before. In this particular case, the corresponding final product obtained was cis-3-[(2-methoxyphenyl)methylamino]-2-benzhydryl-5-ethylquinuclidine (yield, 11%). The free base compound was converted to the hydrochloride salt by dissolving the base in diethyl ether and treating the latter solution with an ethereal solution of hydrogen chloride.

Anal. Calcd. for $C_{30}H_{36}N_2O.0.5HCl$: C, 70.16; H, 7.45; N, 5.45. Found: C, 70.52; H, 7.47; N, 5.03.

EXAMPLE 38

The two-step reaction procedure described in Example 6 was repeated except that 2-benzhydryl-5-ethylquinuclidine-3-one (a product of Preparation C) was the reactant employed in place of 2-[(2,4-dichlorophenyl)phenyl]quinuclidin-3-one, using the same molar proportions as before. In this particular case, the corresponding final product obtained was cis-3-benzylamino-2-benzhydryl-5-ethylquinuclidine. The free base compound was converted to the hydrochloride salt by dissolving the base in diethyl ether and treating the latter solution with an ethereal solution of hydrogen chloride to afford the desired salt product in the form of a semihydrate.

Anal. Calcd. for $C_{29}H_{34}N_2.2HCl.0.5H_2O$: C, 70.72; H, 7.16; N, 5.68. Found: C, 70.85; H, 7.64; N, 5.37.

I claim:

1. A compound that is a substance P receptor antagonist and is selected from quinuclidine derivatives of the formula

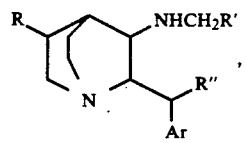

I

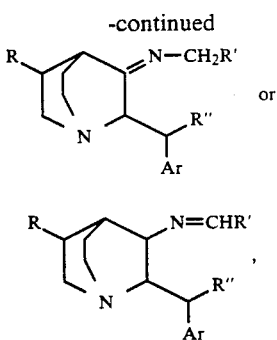

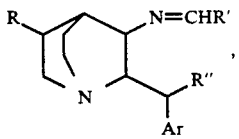

or a pharmaceutically acceptable salt thereof, wherein
Ar is thienyl, phenyl, fluorophenyl, chlorophenyl or bromophenyl;
R is hydrogen or alkyl having from one to four carbon atoms;
R' is cycloalkyl having from five to seven carbon atoms, norbornyl, pyrrolyl, 2,3-dihydrobenzofuranyl, thienyl, alkoxythienyl having from one to three carbon atoms in the alkoxy moiety, pyridyl, hydroxypyridyl, quinolinyl, indolyl, naphthyl, alkoxynaphthyl having from one to three carbon atoms in the alkoxy moiety, biphenyl, 2,3-methylenedioxyphenyl or phenyl substituted with one or two substituents selected from cyano, nitro, amino, N-monoalkylamino having from one to three carbon atoms in the alkyl moiety, fluorine, chlorine, bromine, trifluoromethyl, alkyl having from one to three carbon atoms, alkoxy having from one to three carbon atoms, allyloxy, hydroxy, carboxy, alkoxycarbonyl having from one to three carbons in the alkoxy moiety, benzyloxycarbonyl, carboxybenzyloxy, alkoxycarbonylbenzyloxy having from one to three carbon atoms in the alkoxy moiety, carboxamido and N,N-dialkylcarboxamido having from one to three carbon atoms in the alkyl moiety; and
R" is branched chain alkyl having from three to four carbon atoms, branched chain alkenyl having from five to six carbon atoms, cycloalkyl having from five to seven carbon atoms, furyl, thienyl, pyridyl, indolyl, biphenyl, or phenyl optionally substituted with up to two substituents selected from fluorine, chlorine, bromine, trifluoromethyl, alkyl having from one to three carbon atoms, phenylalkyl having up to three carbon atoms in the alkyl moiety, alkoxy having from one to three carbon atoms, allyloxy, hydroxy, carboxy, alkoxycarbonyl having from one to three carbon atoms in the alkoxy moiety and benzyloxycarbonyl, with the proviso that said R" is always other than unsubstituted phenyl, fluorophenyl, chlorophenyl, bromophenyl or alkylphenyl when said R' is pyrrolyl or thienyl and Ar is other than thienyl.

2. A compound as claimed in claim 1 of the formula I having the cis-configuration.

3. A compound as claimed in claim 1 of the formula II.

4. A compound as claimed in claim 1 of the formula II having the cis-configuration.

5. A compound as claimed in claim 3 wherein Ar is phenyl, R is hydrogen, R' is 2-chlorophenyl and R" is phenyl.

6. A compound as claimed in claim 3 wherein Ar is phenyl, R is hydrogen, R' is 2-trifluoromethylphenyl and R" is phenyl.

7. A compound as claimed in claim 3 wherein Ar is phenyl, R is hydrogen, R' is 2-methoxyphenyl and R" is phenyl.

8. A compound as claimed in claim 4 wherein Ar is phenyl, R is hydrogen, R' is 2-chlorophenyl and R" is phenyl.

9. A compound as claimed in claim 4 wherein Ar is phenyl, R is hydrogen, R' is 2-trifluoromethylphenyl and R" is phenyl.

10. A compound as claimed in claim 4 wherein Ar is phenyl, R is hydrogen, R' is 2-methoxyphenyl and R" is phenyl.

11. A compound as claimed in claim 2 wherein Ar is phenyl, R is hydrogen, R" is substituted phenyl.

12. A compound as claimed in claim 11 wherein R' is phenyl or 2-thienyl.

13. A compound as claimed in claim 12 wherein R" is 3-methoxyphenyl.

14. A compound as claimed in claim 12 wherein R' is phenyl and R" is 4-methoxycarbonylphenyl.

15. A compound as claimed in claim 2 wherein Ar is phenyl, R is hydrogen and R" is furyl or pyridyl.

16. A compound as claimed in claim 2 wherein Ar is phenyl, R is hydrogen and R" is substituted phenyl.

17. A compound as claimed in claim 16 wherein R' is pyridyl or indolyl.

18. A compound as claimed in claim 17 wherein R' is 4-pyridyl.

19. A compound as claimed in claim 17 wherein R' is 3-indolyl.

20. A compound as claimed in claim 16 wherein R' is substituted phenyl.

21. A compound as claimed in claim 20 wherein R' is fluorophenyl, difluorophenyl or chlorophenyl.

22. A compound as claimed in claim 21 wherein R' is 2-chlorophenyl.

23. A compound as claimed in claim 20 wherein R' is trifluoromethylphenyl.

24. A compound as claimed in claim 23 wherein R' is 2-trifluoromethylphenyl.

25. A compound as claimed in claim 20 wherein R' is alkylphenyl or alkoxyphenyl.

26. A compound as claimed in claim 25 wherein R' is 4-methylphenyl.

27. A compound as claimed in claim 25 wherein R' is 2-methoxyphenyl.

28. A compound as claimed in claim 20 wherein R' is alkoxycarbonylphenyl.

29. A compound as claimed in claim 28 wherein R' is 4-methoxycarbonylphenyl.

30. cis-3-[(2-Chlorophenyl)methylamino]-2-benzhydrylquinuclidine.

31. cis-3-[(2-Trifluoromethylphenyl)methylamino]-2-benzhydrylquinuclidine.

32. cis-3-[(2-Methoxyphenyl)methylamino]-2-benzhydrylquinuclidine.

33. A pharmaceutical composition useful for treating gastrointestinal disorders, central nervous system disorders, inflammatory diseases and pain or migraine in mammals, comprising a pharmaceutically acceptable carrier or diluent and a therapeutically-effective amount of a compound as claimed in claim 1.

34. The composition according to claim 33 wherein the compound is of the formula I wherein Ar is phenyl, R is hydrogen, R' is 2-chlorophenyl and R" is phenyl.

35. The composition according to claim 33 wherein the compound is of the formula I wherein Ar is phenyl, R is hydrogen, R' is 2-trifluoromethylphenyl and R" is phenyl.

36. The composition according to claim 33 wherein the compound is of the formula I wherein Ar is phenyl, R is hydrogen, R' is 2-methoxyphenyl and R" is phenyl.

37. A pharmaceutical composition useful for treating gastrointestinal disorders, central nervous system disorders, inflammatory diseases and pain or migraine in a mammal in need of such treatment, comprising a pharmaceutically acceptable carrier or diluent and an amount of a compound as claimed in claim 1 that is effective for antagonizing the effects of substance P at its receptor site in said mammal.

38. A method of treating gastrointestinal disorders, central nervous system disorders, inflammatory diseases and pain or migraine in a mammal in need of such treatment, which comprises administering to said mammal a therapeutically-effective amount of a compound selected from quinuclidine derivatives of the formula:

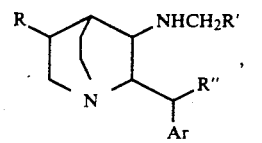

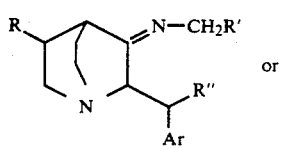

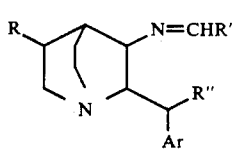

or a pharmaceutically acceptable salt thereof, wherein
Ar is thienyl, phenyl, fluorophenyl, chlorophenyl or bromophenyl;
R is hydrogen or alkyl having from one to four carbon atoms;
R' is cycloalkyl having from five to seven carbon atoms, norbornyl, pyrrolyl, 2,3-dihydrobenzofuranyl, thienyl, alkoxythienyl having from one to three carbon atoms in the alkoxy moiety, pyridyl, hydroxypyridyl, quinolinyl, indolyl, naphthyl, alkoxynaphthyl having from one to three carbon atoms in the alkoxy moiety, biphenyl, 2,3-methylenedioxyphenyl or phenyl optionally substituted with up to two substituents selected from cyano, nitro, amino, N-monoalkylamino having from one to three carbon atoms in the alkyl moiety, fluorine, chlorine, bromine, trifluoromethyl, alkyl having from one to three carbon atoms, alkoxy having from one to three carbon atoms, allyloxy, hydroxy, carboxy, alkoxycarbonyl having from one to three carbons in the alkoxy moiety, benzyloxycarbonyl, carboxybenzyloxy, alkoxycarbonylbenzyloxy having from one to three carbon atoms in the alkoxy moiety, carboxamido and N,N-dialkylcarboxamido having from one to three carbon atoms in the alkyl moiety; and
R" is branched chain alkyl having from three to four carbon atoms, branched chain alkenyl having from five to six carbon atoms, cycloalkyl having from five to seven carbon atoms, furyl, thienyl, pyridyl, indolyl, biphenyl, or phenyl optionally substituted with up to two substituents selected from fluorine, chlorine, bromine, trifluoromethyl, alkyl having from one to three carbon atoms, phenylalkyl having up to three carbon atoms in the alkyl moiety, alkoxy having from one to three carbon atoms, allyloxy, hydroxy, carboxy, alkoxycarbonyl having from one to three carbon atoms in the alkoxy moiety or benzyloxycarbonyl.

39. The method as claimed in claim 38 wherein said compound administered is of the formula I.

40. The method as claimed in claim 38 wherein said compound administered is of the formula II.

41. The method as claimed in claim 38 wherein said compound administered is of the formula III.

42. The method as claimed in claim 41 wherein said compound administered is cis-3-[(2-chlorophenyl)methylamino]-2-benzhydrylquinuclidine.

43. The method as claimed in claim 41 wherein said compound administered is cis-3-[(2-trifluorophenyl)methylamino]-2-benzhydrylquinuclidine.

44. The method as claimed in claim 41 wherein said compound administered is cis-3-[(2-methoxyphenyl)methylamino]-2-benzhydrylquinuclidine.

45. The method as claimed in claim 41 wherein said compound administered is cis-3-[(2-thienyl)methylamino]-2-benzhydrylquinuclidine.

46. A method for antagonizing substance P in the treatment of gastrointestinal disorders, central nervous system disorders, inflammatory diseases and pain or migraine in a mammal in need of such treatment, which comprises administering to said mammal a compound as claimed in claim 38 in an amount that is effective for antagonizing the effects of substance P at its receptor site in said mammal.

47. A radioactive isotope of a compound as claimed in claim 1, said radioactive isotope being selected from the group consisting of the tritium and $C^{14}$-isotopes of said compound.

48. A radioactive isotope as claimed in claim 47 wherein said radioactive isotope is a tritium or $C^{14}$-isotope of (−)-cis-3-[(2-methoxyphenyl)methylamino]-2-benzhydrylquinuclidine.

* * * * *